(12) United States Patent
Gorman, III et al.

(10) Patent No.: US 12,310,849 B2
(45) Date of Patent: *May 27, 2025

(54) VALVE PROSTHESIS

(71) Applicant: MAJORO CARDIAC INNOVATIONS, LLC, Marco Island, FL (US)

(72) Inventors: Joseph H. Gorman, III, Lower Gwynedd, PA (US); Robert C. Gorman, Lower Gwynedd, PA (US); Matthew J. Gillespie, Bryn Mawr, PA (US)

(73) Assignee: MAJORO CARDIAC INNOVATIONS, LLC, Marco Island, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/301,399

(22) Filed: Apr. 17, 2023

(65) Prior Publication Data
US 2023/0248517 A1     Aug. 10, 2023

Related U.S. Application Data

(63) Continuation of application No. 16/656,787, filed on Oct. 18, 2019, now Pat. No. 11,628,060, which is a
(Continued)

(51) Int. Cl.
*A61F 2/24* (2006.01)

(52) U.S. Cl.
CPC .............. *A61F 2/2418* (2013.01); *A61F 2/24* (2013.01); *A61F 2/2409* (2013.01);
(Continued)

(58) Field of Classification Search
CPC ........ A61F 2/24; A61F 2/2409; A61F 2/2418; A61F 2/2436; A61F 2210/0004;
(Continued)

(56) References Cited

U.S. PATENT DOCUMENTS

| 5,685,306 A | 11/1997 | Davidson |
| 5,957,949 A | 9/1999 | Leonhardt et al. |

(Continued)

FOREIGN PATENT DOCUMENTS

| DE | 102005052628 A1 | 5/2007 |
| DE | 102006052564 B3 | 12/2007 |

(Continued)

OTHER PUBLICATIONS

Boudjemline et al., "Steps toward the percutaneous replacement of atrioventricular valves an experimental study", J. Am. Coll. Cardiol., Jul. 19, 2005, 46(2), 360-365.

(Continued)

*Primary Examiner* — Dinah Baria
(74) *Attorney, Agent, or Firm* — MH2 Technology Law Group, LLP

(57) ABSTRACT

The present disclosure relates to valve replacement devices that are foldable for catheter-based deployment to the site of implantation, as well as systems for the delivery of valve prostheses, including prostheses having the special characteristics of the disclosed valve replacement devices. The devices include highly effective adhering mechanisms for secure and enduring precision implantation. The adhering mechanisms may employ a unique sealing mechanism that includes a cuff that expands slowly whereby the device is not secured in place until the completion of the implantation procedure. The implanted device, optionally together with the cuff, prevents perivalvular leaks and incorporate an appropriate leaflet system for reliable functioning in situ.

22 Claims, 10 Drawing Sheets

Related U.S. Application Data continuation of application No. 15/074,451, filed on Mar. 18, 2016, now abandoned, which is a continuation of application No. 15/015,736, filed on Feb. 4, 2016, now abandoned, which is a continuation of application No. 13/505,885, filed as application No. PCT/US2010/055645 on Nov. 5, 2010, now Pat. No. 9,289,291.

(60) Provisional application No. 61/258,331, filed on Nov. 5, 2009.

(52) U.S. Cl.
CPC .... *A61F 2/2436* (2013.01); *A61F 2210/0004* (2013.01); *A61F 2210/0014* (2013.01); *A61F 2210/0061* (2013.01); *A61F 2210/0076* (2013.01); *A61F 2220/0008* (2013.01); *A61F 2230/0054* (2013.01); *A61F 2230/0058* (2013.01); *A61F 2230/0078* (2013.01); *A61F 2250/003* (2013.01); *A61F 2250/0039* (2013.01); *A61F 2250/0069* (2013.01)

(58) Field of Classification Search
CPC ...... A61F 2210/0076; A61F 2210/0014; A61F 2220/0008; A61F 2230/0054; A61F 2250/0039
See application file for complete search history.

(56) References Cited

U.S. PATENT DOCUMENTS

| | | |
|---|---|---|
| 6,398,758 B1 | 6/2002 | Jacobsen et al. |
| 6,551,302 B1 | 4/2003 | Rosinko et al. |
| 6,669,719 B2 | 12/2003 | Wallace et al. |
| 6,790,229 B1 | 9/2004 | Berreklouw |
| 6,790,230 B2 | 9/2004 | Beyersdorf et al. |
| 7,270,675 B2 | 9/2007 | Chun et al. |
| 7,335,218 B2 | 2/2008 | Wilson et al. |
| 7,338,467 B2 | 3/2008 | Lutter |
| 8,236,049 B2 | 8/2012 | Rowe et al. |
| 8,252,051 B2 | 8/2012 | Chau et al. |
| 8,323,336 B2 | 12/2012 | Hill et al. |
| 8,449,599 B2 | 5/2013 | Chau et al. |
| 8,579,964 B2 | 11/2013 | Lane et al. |
| 8,585,755 B2 | 11/2013 | Chau et al. |
| 8,828,078 B2 | 9/2014 | Salahieh et al. |
| 9,289,291 B2 | 3/2016 | Gorman et al. |
| 2001/0021872 A1 | 9/2001 | Bailey et al. |
| 2003/0009213 A1 | 1/2003 | Yang |
| 2003/0023303 A1 | 1/2003 | Palmaz et al. |
| 2004/0106976 A1 | 6/2004 | Bailey et al. |
| 2005/0137688 A1 | 6/2005 | Salahieh et al. |
| 2005/0137691 A1 | 6/2005 | Salahieh et al. |
| 2006/0020334 A1 | 1/2006 | Lashinski et al. |
| 2006/0058872 A1 | 3/2006 | Salahieh et al. |
| 2006/0195183 A1 | 8/2006 | Navia et al. |
| 2006/0224183 A1 | 10/2006 | Freudenthal |
| 2006/0259135 A1 | 11/2006 | Navia et al. |
| 2007/0016286 A1 | 1/2007 | Herrmann et al. |
| 2007/0142906 A1 | 6/2007 | Figulla et al. |
| 2007/0213813 A1 | 9/2007 | Von et al. |
| 2007/0239265 A1 | 10/2007 | Birdsall |
| 2007/0244544 A1 | 10/2007 | Birdsall et al. |
| 2008/0183130 A1 | 7/2008 | Lutter |
| 2008/0188928 A1 | 8/2008 | Salahieh et al. |
| 2008/0215144 A1 | 9/2008 | Ryan et al. |
| 2008/0221672 A1 | 9/2008 | Lamphere et al. |
| 2008/0228263 A1 | 9/2008 | Ryan |
| 2008/0243151 A1 | 10/2008 | Binmoeller et al. |
| 2008/0275540 A1 | 11/2008 | Wen |
| 2009/0005863 A1 | 1/2009 | Goetz et al. |
| 2009/0112309 A1 | 4/2009 | Jaramillo et al. |
| 2009/0222076 A1 | 9/2009 | Figulla et al. |
| 2010/0036479 A1 | 2/2010 | Hill et al. |
| 2010/0298931 A1 | 11/2010 | Quadri et al. |
| 2010/0312333 A1 | 12/2010 | Navia et al. |

FOREIGN PATENT DOCUMENTS

| | | | |
|---|---|---|---|
| EP | 2047824 | A1 | 4/2009 |
| JP | 2000-037403 | A | 2/2000 |
| JP | 2003-518984 | A | 6/2003 |
| JP | 2008-526379 | A | 7/2008 |
| JP | 2009-514628 | A | 4/2009 |
| WO | 2006/076325 | A1 | 7/2006 |
| WO | 2006/089236 | A1 | 8/2006 |
| WO | 2006/113906 | A1 | 10/2006 |
| WO | 2006/138173 | A2 | 12/2006 |
| WO | 2007/051620 | A1 | 5/2007 |
| WO | 2007/081820 | A1 | 7/2007 |
| WO | 2007/149933 | A2 | 12/2007 |
| WO | 2008/028569 | A1 | 3/2008 |
| WO | 2008/031103 | A2 | 3/2008 |
| WO | 2008/035337 | A2 | 3/2008 |
| WO | 2008/070797 | A2 | 6/2008 |
| WO | 2008/089365 | A2 | 7/2008 |
| WO | 2008/095475 | A2 | 8/2008 |
| WO | 2009/132187 | A1 | 10/2009 |
| WO | 2010/057262 | A8 | 7/2010 |
| WO | 2010/112844 | A1 | 10/2010 |
| WO | 2010/127041 | A1 | 11/2010 |
| WO | 2011/069048 | A2 | 6/2011 |
| WO | 2011/106533 | A1 | 9/2011 |
| WO | 2011/137531 | A1 | 11/2011 |
| WO | 2012/011108 | A2 | 1/2012 |

OTHER PUBLICATIONS

Definition of "enfold"; https://www.google.com/search?q=define+enfold&rlz=1C1GCEA_en&oq=define&aqs=chrome.0.69i59l3j69i57j0i10i433i512j0i10i131l1433i512j0i10i433i512j0i5l213.17024j0j1&sourceid=chrome&ie=UTF-8.

Dwivedi et al., "Reference values for mitral and tricuspid annular dimensions using two-dimensional echocardiography", Echo Research and Practice, Dec. 2014, 1(2), 43-50.

European Patent Application No. 10829157.6; Extended Search Report; dated Apr. 5, 2016; 13 pages.

https://www.ncbi.nlm.nih.gov/pmc/articles/PMC4676479/, Reference values for mitral and tricuspid annular dimensions using two-dimensional echocardiography, Sep. 24, 2014, Queen Elizabeth Hospital, University Hospital Birmingham NHS Foundation Trust, Mindelsohn Way, Edgbaston, Birmingham, B15 2WB, UK (Year: 2014).

International Patent Application No. PCT/US2010/055645: International Search Report and Written Opinion dated Jan. 10, 2011, 9 pages.

Lozonschi et al., Transapical mitral valved stent implantation, Ann Thorac Surg., 2008, Sep. 86(3), 745-748.

Ma et al., "Double-Crowned Valved Stents for off-pump mitral valve replacement", Eur. J. Cardiothorac Surg., Aug. 2005, 28(2), 194-198.

U.S. Appl. No. 15/425,915.

VALVE PROSTHESIS

CROSS-REFERENCE TO RELATED APPLICATION

This application is a continuation of U.S. Ser. No. 16/656,787, filed Oct. 18, 2019 (now U.S. Pat. No. 11,628,060, issued Apr. 18, 2023), which is a continuation of U.S. Ser. No. 15/074,451, filed Mar. 18, 2016, which is a continuation of U.S. Ser. No. 15/015,736, filed on Feb. 4, 2016, which is a continuation of U.S. Ser. No. 13/505,885, filed on Aug. 7, 2012 (now U.S. Pat. No. 9,289,291, issued on Mar. 22, 2016), which is the National Stage of International Application No. PCT/US2010/055645, filed Nov. 5, 2010, which claims the benefit of U.S. Provisional Application No. 61/258,331 filed Nov. 5, 2009, the entire disclosures of each of which are incorporated herein by reference.

TECHNICAL FIELD

The present disclosure relates to anatomical valve replacement devices and methods and systems for replacing a valve and for delivering a stented device.

BACKGROUND

The mitral valve is a complex structure whose competence relies on the precise interaction of annulus, leaflets, chordae, papillary muscles and left ventricle (LV). Pathologic changes in any of these structures can lead to valvular insufficiency. Myxomatous leaflet/chordal degeneration, and dilated ischemic cardiomyopathy secondary to chronic post infarction ventricular remodeling are among most common mechanisms producing mitral regurgitation (MR). These two disease processes account for about 78% of all cases of MR treated surgically.

As part of the Framingham Heart Study, the prevalence of mitral valve prolapse in Framingham, MA was estimated at 2.4%. There was a near-even split between classic and non-classic MVP, with no significant age or sex discrimination. Based on data gathered in the United States, MVP is prevalent in 7% of autopsies. The incidence of mitral regurgitation increases with age and is a frequent clinically significant medical problem in the post MI population and patients with COPD.

The use of a catheter based percutaneous valved stent has been shown to be feasible in replacing both the human pulmonic and aortic valves. The pulmonic valve was the first to be successfully replaced by a percutaneous approach and is the furthest along in development. There are currently two aortic valve products in clinical trials and more in development. While there is a great deal of interest in replacing the mitral valve percutaneously (not least because many patients that have suffered myocardial infarction are not fit for surgical valve replacement) the anatomy and function of the mitral valve prevents direct application of the current aortic/pulmonic technology. However, there have been recent efforts towards developing mitral valve replacements that have focused on transapical valved stent implantation (see Lozonschi L, et al., Transapical mitral valved stent implantation. *Ann Thorac Surg.* 2008 September; 86(3):745-8); "double-crown" valved stent designs (see Ma L, et al., *Double-crowned valved stents for off-pump mitral valve replacement. Eur J Cardiothorac Surg.* 2005 August; 28(2): 194-8); and, valved stent designs consisting of two disks separated by a cylinder (see Boudjemline Y, et al., *Steps toward the percutaneous replacement of atrioventricular valves an experimental study. J Am Coll Cardiol.* 2005 Jul. 19; 46(2):360-5).

It has presently been discovered that a successful percutaneously placed valve requires four major design characteristics. The valve must be compatible with acceptable delivery modalities, it must anchor to the valvular ring and seal the anchor point to prevent leaks, and the valve must function normally when in place. Among publicly available designs, there does not presently exist a percutaneous valved stent having the characteristics that are believed to be necessary for successful implantation, stability, and long-term functionality. A design having such characteristics would have profound medical implications both for those newly in need of valve replacement, and among patients that are currently fitted with conventional valve designs.

SUMMARY

In one aspect, valve prostheses are provided comprising a self-expanding stent comprising an outer surface, an interior surface, a middle region, an upper anchoring flange, and a lower anchoring flange, wherein the stent has an unexpanded and an expanded state; a cuff comprising an absorbent material disposed at least partially circumferentially around the outer surface of the stent, wherein the absorbent material expands by absorption of a fluid to substantially adhere the prosthesis at an implantation site, and wherein the adhering is delayed for a time sufficient to permit positioning of the prosthesis at the implantation site; and a valve comprising at least two leaflets fixedly attached to the interior surface of the stent.

In another aspect, methods are disclosed for replacing a damaged or diseased valve in a subject comprising: delivering to an implantation site of the subject a mitral valve prosthesis comprising a self-expanding stent comprising an outer surface, an interior surface, a middle region, an upper anchoring flange, and a lower anchoring flange, wherein the stent has an unexpanded and an expanded state; a cuff comprising an absorbent material disposed at least partially circumferentially around the outer surface of the stent and a valve comprising at least two leaflets fixedly attached to the interior surface of the stent; and expanding the cuff by absorption of a fluid to substantially adhere the prosthesis at an implantation site, wherein the adhering is delayed for a time sufficient to permit positioning of the prosthesis at the implantation site.

Also disclosed are valve prostheses comprising an at least partially self-expanding stent comprising a wire framework defining outer and interior surfaces, and upper and lower anchoring flanges interposed by a middle region, the stent having an unexpanded and an expanded state, and the lower anchoring flange having at least one geometric dimension that is greater than the corresponding dimension of the upper anchoring flange; and a valve comprising at least one leaflet fixedly attached to the interior surface of the stent.

The present disclosure also includes methods for replacing a damaged or diseased valve in a subject comprising: delivering to an implantation site of the subject a valve prosthesis comprising an at least partially self-expanding stent comprising a wire framework defining outer and interior surfaces, and upper and lower anchoring flanges interposed by a middle region, the stent having an unexpanded and an expanded state, and the lower anchoring flange having at least one geometric dimension that is greater than the corresponding dimension of the upper anchoring flange; and a valve comprising at least one leaflet fixedly attached to the interior surface of the stent; and expanding the stent to substantially adhere the prosthesis at the implantation site.

In another aspect, provided are systems for delivering a valve prosthesis comprising an at least partially self-expanding stent to an implantation site comprising: a catheter comprising a distal end and a proximal end, a guidewire lumen to permit the catheter to be translated along a guidewire, a steering lumen for accommodating a tension cable for steering the catheter, and a dock at the distal end onto which the stent may be loaded. The present systems also comprise a retractable compression sleeve for compressing at least a portion of the stent while the stent is loaded onto the dock; a leading tip positioned distal to the dock for leading the catheter during delivery; and, a steering mechanism operably associated with the tension cable for deflecting the leading tip in at least one directional plane.

In yet another aspect, there are disclosed kits comprising a system comprising an at least partially self-expanding stent to an implantation site comprising: a catheter comprising a distal end and a proximal end, a guidewire lumen to permit the catheter to be translated along a guidewire, a steering lumen for accommodating a tension cable for steering the catheter, and, a dock at the distal end onto which the stent may be loaded; a retractable compression sleeve for compressing at least a portion of the stent while the stent is loaded onto the dock; a leading tip positioned distal to the dock for leading the catheter during delivery; and, a steering mechanism operably associated with the tension cable for deflecting the leading tip in at least one directional plane; and, at least one valve prosthesis comprising an at least partially self-expanding stent comprising a wire framework defining outer and interior surfaces, and upper and lower anchoring flanges interposed by a middle region, the stent having an unexpanded and an expanded state, and the lower anchoring flange having at least one geometric dimension that is greater than the corresponding dimension of the upper anchoring flange; and a valve comprising at least one leaflet fixedly attached to the interior surface of the stent.

The present disclosure also pertains to methods for delivering a valve prosthesis comprising an at least partially self-expanding stent to an implantation site comprising: (i) providing a system comprising a catheter comprising a distal end and a proximal end, a guidewire lumen to permit the catheter to be translated along a guidewire, a steering lumen for accommodating a tension cable for steering the catheter, and, a dock at the distal end onto which the stent may be loaded; a retractable compression sleeve for compressing at least a portion of the stent while the stent is loaded onto the dock; a leading tip positioned distal to the dock for leading the catheter during delivery; and, a steering mechanism operably associated with the tension cable for deflecting the leading tip in at least one directional plane; (ii) loading onto the dock the valve prosthesis; (iii) delivering a guidewire to the implantation site; (iv) translating the catheter over the guidewire so that the loaded valve prosthesis is positioned at the implantation site; (v) retracting the retractable compression sleeve to permit the stent to expand at the implantation site and to undock from the catheter; and, (vi) removing the catheter and the guidewire from the implantation site.

BRIEF DESCRIPTION OF THE DRAWINGS

The foregoing and other aspects of the present inventions will become apparent from the following detailed description when considered in conjunction with the accompanying drawings. For the purpose of illustrating the invention, there is shown in the drawings embodiments that are presently preferred, it being understood, however, that the invention is not limited to the specific aspects disclosed. The drawings are not necessarily drawn to scale. In the drawings.

DETAILED DESCRIPTION OF ILLUSTRATIVE EMBODIMENTS

Figure 1:
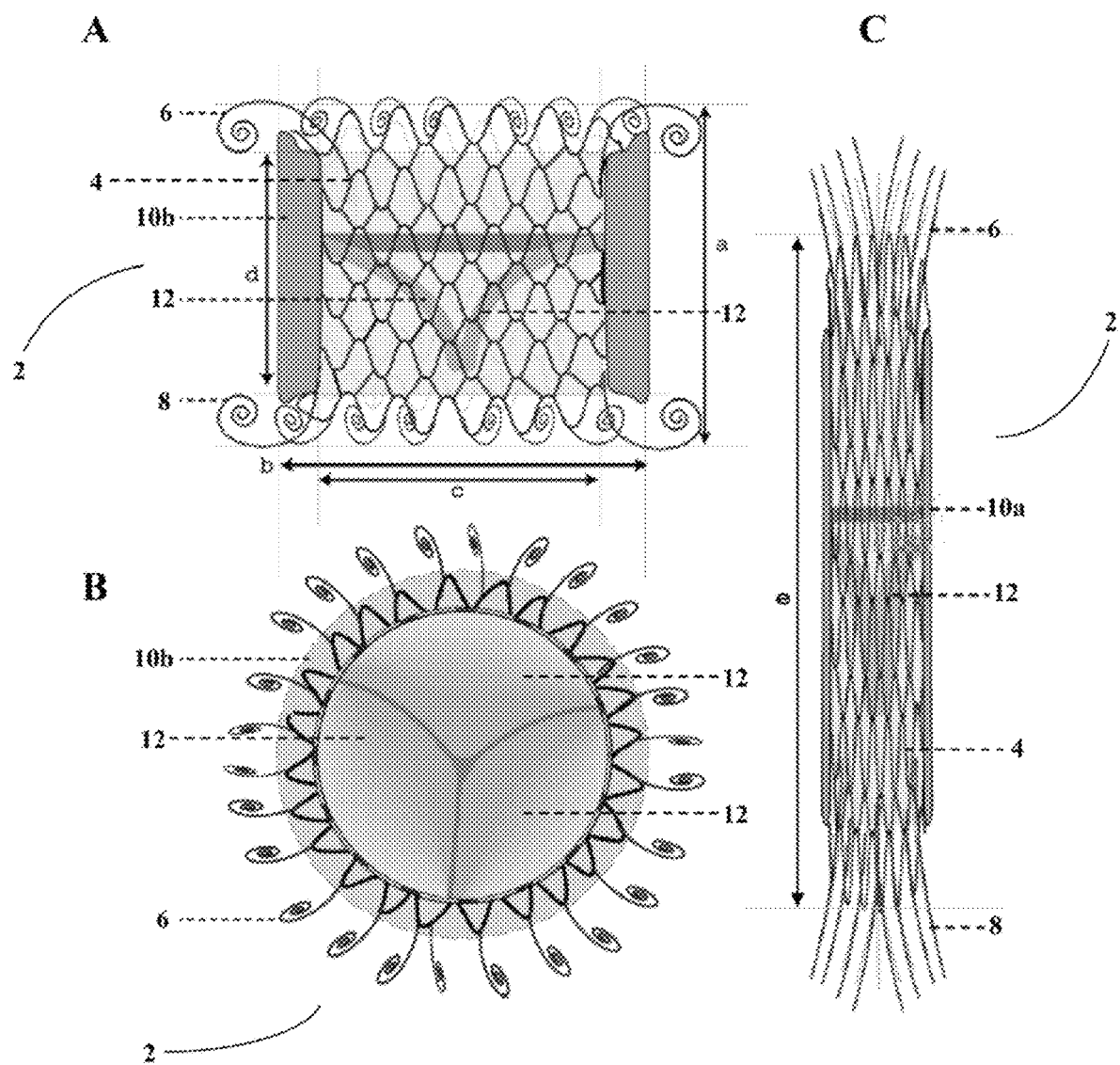
FIG. 1 shows three different views of an exemplary prosthesis according to the present disclosure.

The present inventions may be understood more readily by reference to the following detailed description taken in connection with the accompanying figures and examples, which form a part of this disclosure. It is to be understood that these inventions are not limited to the specific products, methods, conditions or parameters described and/or shown herein, and that the terminology used herein is for the purpose of describing particular embodiments by way of example only and is not intended to be limiting of the claimed inventions.

In the present disclosure the singular forms "a," "an," and "the" include the plural reference, and reference to a particular numerical value includes at least that particular value, unless the context clearly indicates otherwise. Thus, for example, a reference to "a material" is a reference to one or more of such materials and equivalents thereof known to those skilled in the art, and so forth. When values are expressed as approximations, by use of the antecedent "about," it will be understood that the particular value forms another embodiment. As used herein, "about X" (where X is a numerical value) preferably refers to ±10% of the recited value, inclusive. For example, the phrase "about 8" preferably refers to a value of 7.2 to 8.8, inclusive; as another example, the phrase "about 8%" preferably (but not always) refers to a value of 7.2% to 8.8%, inclusive. Where present, all ranges are inclusive and combinable. For example, when a range of "1 to 5" is recited, the recited range should be construed as including ranges "1 to 4", "1 to 3", "1-2", "1-2 & 4-5", "1-3 & 5", "2-5", and the like. In addition, when a list of alternatives is positively provided, such listing can be interpreted to mean that any of the alternatives may be excluded, e.g., by a negative limitation in the claims. For example, when a range of "1 to 5" is recited, the recited range may be construed as including situations whereby any of 1, 2, 3, 4, or 5 are negatively excluded; thus, a recitation of "1 to 5" may be construed as "1 and 3-5, but not 2", or simply "wherein 2 is not included."

Unless otherwise specified, any component, element, attribute, or step that is disclosed with respect to one aspect of the present invention (for example, the prostheses, systems, kits, and methods, respectively) may apply to any other aspect of the present invention (any other of the rostheses, systems, kits, and methods, respectively) that is disclosed herein The disclosures of each patent, patent application, and publication cited or described in this document are hereby incorporated herein by reference, in their entirety.

It has previously been demonstrated that the use of catheter-based percutaneous valved stents is feasible for the replacement of both of human pulmonic and human aortic valves. Replacement of the pulmonic valve was the first to be successfully performed using a percutaneous approach, and is presently the furthest along in development. While there is a great deal of interest in replacing the mitral valve percutaneously, the anatomy and function of the mitral valve prevents direct application of the technology that is currently applicable to pulmonic and aortic valve replacement. There are presently a significant number of patients that suffer from mitral valve incompetence due to left ventricular dysfunction after a myocardial infarction. However, many of these patients are deemed too fragile to undergo surgical mitral valve replacement or repair. The development of a catheter-based technology for reliable replacement of the mitral valve would allow such patients to be included among those subjects who are eligible for life-saving mitral valve replacement therapy. It has presently been discovered that successful percutaneously delivered valve should possess four main design characteristics: it must be foldable or collapsible for delivery; it must anchor to the valvular ring; it must seal the implantation point to prevent leaks; and, the valve itself must function normally when in situ. The presently disclosed valve replacements are foldable for catheter-based deployment to the site of implantation, include highly effective anchoring mechanisms for secure and enduring precision implantation, employ unique sealing mechanisms that prevents perivalvular leaks, and incorporates an appropriate leaflet system for reliable functioning in situ.

General Embodiment I

The following disclosure pertains to a first general embodiment of the present disclosure, which pertains to inventive valve prostheses and methods for replacing a damaged or diseased valve.

In one aspect, valve prostheses are provided comprising a self-expanding stent comprising an outer surface, an interior surface, a middle region, an upper anchoring flange, and a lower anchoring flange, wherein the stent has an unexpanded and an expanded state; a cuff comprising an absorbent material disposed at least partially circumferentially around the outer surface of the stent, wherein the absorbent material expands by absorption of a fluid to substantially adhere the prosthesis at an implantation site, and wherein the anchoring is delayed for a time sufficient to permit positioning of the prosthesis at the implantation site; and a valve comprising at least two leaflets fixedly attached to the interior surface of the stent. In preferred embodiments, the prosthesis is a mitral valve prosthesis.

The stent may be self-expanding, or may be configured to be forcibly expanded, for example, by a balloon. In preferred embodiments, the stent is self-expanding. The self-expanding stent preferably comprises a shape-memory or "superelastic" material exhibiting large elastic strains. An exemplary material is nitinol, a nickel-titanium alloy. Any other material possessing similar characteristics may also be used in the construction of the self-expanding stent, and more generally, and suitable, biocompatible material may be used to form the stent, whether it is self-expanding or not. Exemplary materials include stainless steel, cobalt/chromium alloy, cobalt/chromium/nickel alloy, nickel/chromium alloy, platinum, platinum/iridium alloy, among others. The stent may comprise one or more other materials that are themselves not self-expanding but that do not inhibit or otherwise interfere with the ability of the stent to self-expand. For example, any biocompatible material may be included to add any other desired structural feature to the stent. Exemplary biocompatible materials include stainless steel, tantalum, platinum alloys, niobium alloys, and cobalt alloys, among others. Additionally or alternatively, one or more bioabsorbable materials may be used in forming the stent. Part or all of the stent may be coated with a composition comprising a drug, so that the stent is capable of eluting drug in situ. The stent preferably comprises a framework that is formed from the material that allows the stent to be self-expanding, in addition to any other compatible materials as described above. The structural framework can be formed from wire using conventional techniques, such as coiling, weaving, braiding, or knitting. The wire may be welded or otherwise joined at some or all crossover points, thereby forming a structure that is not hinged. The formation of stents is readily appreciated among those skilled in the art and the present disclosure is intended to embrace any suitable technique, including any functionally acceptable stent geometry.

The stent comprises a middle region having various dimensions, including an unexpanded length, an unexpanded outer circumference, an expanded length, and an expanded outer circumference. The unexpanded length is preferably substantially the same as or greater than the expanded length, and the expanded outer circumference is greater than the unexpanded outer circumference. The unexpanded outer circumference may be any size that enables the unexpanded stent to be translated through the interior of a catheter. For example, the unexpanded outer circumference may be of a size that enables the unexpanded stent to be translated along the interior of a catheter having a diameter of about 1 mm to about 8 mm. The expanded length preferably substantially corresponds to the length that is about the same as or longer than that of the annulus between the left atrium and left ventricle of a human subject's heart. Preferably, the expanded length of the stent is longer than that of the annulus between the left atrium and left ventricle. Because the length of the mitral valve annulus may vary from subject to subject, a particular subject may be matched with a stent having an expanded length that is appropriate for the mitral valve annulus of that subject. In general, the expanded length may be about 0.5 cm to about 5 cm, about 1 cm to about 4 cm, about 1.5 cm to about 3.5 cm, or about 2 cm to about 3 cm. The expanded outer circumference may be substantially the same as or less than the inner circumference of a subject's mitral valve annulus. In preferred embodiments, the expanded outer circumference is less than the inner circumference of a subject's mitral valve annulus, and is appropriately sized such that the stent having a cuff that is disposed at least partially circumferentially around the outer surface of the stent can be positioned within the mitral valve annulus. As discussed more fully herein, the cuff has an unexpanded form and an expanded form, and the stent is preferably appropriately sized such that the stent having a substantially unexpanded cuff disposed at least partially circumferentially around the outer surface of the stent can be positioned within the mitral valve. In general, the expanded outer circumference of the stent may be about 2 cm to about 5 cm, about 2.5 cm to about 4 cm, or about 2.5 cm to about 3.5 cm.

The prostheses according to the present disclosure may be configured to be delivered transatrially, transapically, or percutaneously. Thus, the dimensions of the prosthesis, the type of material used for the stent, cuff, or other components, the presence or absence of a drug coating on the stent, the type of flanges that are included, the weave pattern of the stent, the length of delay of absorption of fluid, and other factors may all be manipulated in order to configure the prosthesis for transatrial, transapical, or percutaneous delivery, as desired. Those skilled in the art will readily appreciate the characteristics that are required for delivery of a stented device by the transatrial, transapical, or percutaneous route, respectively, and may select accordingly from the wide range of characteristics described herein.

Figure 2:
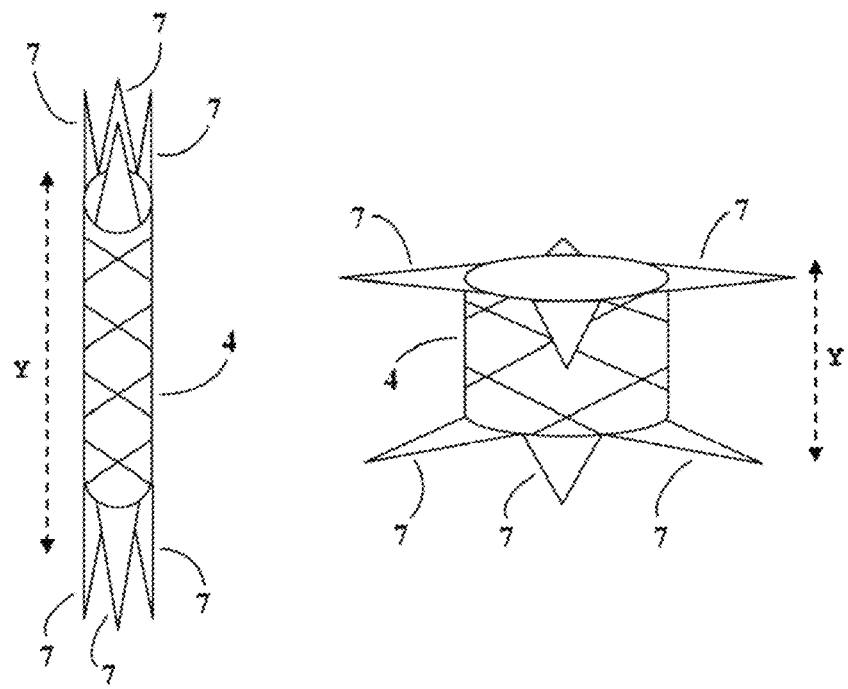
FIG. 2 depicts a simplified version of an exemplary prosthesis featuring upper and lower flanges that comprise projections.

In addition to the middle region the self-expanding stent comprises an upper and a lower flange. In the most simple embodiment, one or both of the flanges comprise the longitudinal ends or margins of the middle region. For example, one or both of the flanges may be a "lip" of material that extends partly or fully around the circumference of the stent at a longitudinal end of the middle region. In other embodiments, one or both of the flanges may be configured to provide an anchoring functionality that substantially affixes the stent at the location of the mitral annulus. In particular, one of the upper or lower flanges may be configured to anchor to the ventricular side of the mitral annulus, and the other of the upper or lower flanges may be configured to anchor the atrial side of the mitral annulus. The upper flange, lower flange, or both may comprise a plurality of protruding stent elements. For example, if the stent is constructed from wire, the flanges may comprise a plurality of individual wires or bundled sets of wires. The plurality of wires may comprise a regularly or irregularly spaced array, and the wires themselves may be present as single strands, or as grouped or bundled sets of two, three, four, or more wire strands. Each flange may have a configuration that corresponds to the unexpanded state of the stent, and a configuration that corresponds to the expanded state of the stent. When one or both of the flanges comprise a plurality of individual stent elements, the elements may be substantially straightened when the stent is in the unexpanded state and may be substantially coiled when the stent is in the unexpanded state. In other embodiments, a flange may comprise one or more elements that define flaps, lobes, or other projections that may be oriented substantially parallel with the long axis of the stent when the stent is in an unexpanded state and oriented at a substantially oblique angle (for example, about 30°, about 45°, about 60°, about 75°, or about 90°) relative to the long axis of the stent when the stent is in an expanded state. FIG. 2 provides a simplified view of an exemplary embodiment of this variety, having flaps 7 that are oriented substantially parallel with the long axis Y when stent 4 is in an unexpanded state (FIG. 2A) and that are oriented at a substantially oblique angle relative to the "long" axis Y when stent 4 is an expanded state. Any flange design, whether consisting of a unitary structure or numerous discrete elements, is contemplated for purposes of the present disclosure.

The present mitral valve prostheses also comprise a cuff comprising an absorbent material that is disposed at least partially circumferentially around the outer surface of the stent. The term "cuff" is intended to embrace a continuous ring of absorbent material that forms a complete circle around the outer surface of the stent; any other conformation that involves a contiguous portion of absorbent material, such as a strip that forms a spiral around the outer surface of the stent; one, two, three or more disparate patches or strips (or any other shape or configuration) of absorbent material disposed on the outer surface of the stent; or, any combination of one or more contiguous portions of material and disparate patches, strips, and the like. In a preferred embodiment, the cuff comprises a continuous ring of absorbent material that forms a complete circle around the outer surface of the stent.

The cuff comprises an absorbent material that expands by absorption of a fluid to substantially adhere the prosthesis at the implantation site. When the disclosed prostheses are used to replace a damaged or nonfunctional mitral valve, the implantation site is the mitral valve annulus. As used herein to "adhere" may mean to substantially affix or anchor the prosthesis at the implantation site, to create a seal between the cuff and the mitral valve annulus that is substantially impermeable to fluid, or both. It has been presently discovered that the cuff can form a seal that reliably prevents perivalvular leakage between the atrium and ventricle, such that when the prosthesis is in place, the only fluid that passes between the atrium and ventricle is that which is allowed to pass by the activity of the replacement valve itself.

The adhering of the prosthesis is delayed for a time sufficient to permit positioning of the prosthesis at the implantation site. For example, because the procedure for positioning the prosthesis via a catheter at the implantation site may last 40 minutes, the expansion by the cuff by absorption of fluid to a sufficient degree such as to adhere the prosthesis to the implantation may be delayed until that time has elapsed. Thus, the cuff comprises one or more materials, components, or both that creates a delay in the absorption of fluid or that provides a sufficiently slow rate of absorption of the fluid, such that the cuff does not expand to the degree required to adhere the prosthesis to the implantation site until the desired period of delay has elapsed. The period of delay may be measured starting at the point in time where the prosthesis is exposed to a fluid (e.g., blood). The delay period may be about 1 minute, about 2 minutes, about 5 minutes, about 7 minutes, about 10 minutes, about 15 minutes, about 20 minutes, about 30 minutes, about 45 minutes, about 1 hour, about 75 minutes, about 90 minutes, or about 2 hours. The type of cuff that is selected for use with the prosthesis may depend on the difficulty of the procedure to deliver the prosthesis to the implantation site.

The absorbent material of the cuff may itself absorb fluid at a sufficiently slow rate to delay the adhering of the prosthesis at the implantation site. In other embodiments, the absorbent material of the cuff may feature a variable rate of absorption, such that the rate of absorption is low for an initial period of time but that increases over time or after a period of time. For example, the absorbent material may have a fluid absorption rate of about 0 µL to about 20 µL per minute for a first period of time following exposure of the prosthesis to the fluid, and a fluid absorption rate from about 10 to about 200 µL per minute after the first period of time. The period of time after which the rate of absorption increases may be about 10 minutes, about 15 minutes, about 20 minutes, about 30 minutes, about 45 minutes, about 1 hour, about 90 minutes, about 2 hours, about 180 minutes, or about 2 hours. In other embodiments, the ability of the absorbent material of the cuff to absorb fluid is delayed. For example, the absorbent material of the cuff may be completely or partially covered with or contained within a material that affects the ability of the absorbent material to absorb fluid. The absorbent material may be completely or partially covered with or contained within a cover material, e.g., a film or fabric, that is permanently impermeable to fluid, but that is removable and is removed when the desired period of delay has elapsed; the removal of the cover material may be effected while the prosthesis is in situ at the implantation site, for example, by using a catheter-based removal tool to grasp and remove the cover material. Any material that is substantially impermeable to fluid (such as water, blood, and the like) and that is biocompatible may be used to form the cover material. Nonlimiting examples include polyurethanes, polyethylenes, polydimethylsiloxane, silicones, rubbers, and polyvinyl chloride. In other embodiments, the absorbent material may be completely or partially covered with or contained within a cover material, e.g., a film or fabric, that is temporarily impermeable to fluid, but that becomes permeable to fluid after a desired period of delay. For example, the cover material may be degradable over time, or may comprise a material that degrades or is altered in response to a change in temperature, pH, or some other environmental cue that is present at the implantation site. In other embodiments, the absorbent material may be completely or partially covered with or contained within a cover material that is permeable to fluid, but the transfer of fluid across such cover material and/or saturation of by the cover material by fluid is sufficiently slow to provide a delay before the absorbent material absorbs a sufficient amount of fluid to adhere to the implantation site. The period of delay that is provided by a cover material may be, for example, about 5 minutes to about 3 hours, about 10 minutes to about 3 hours, about 20 minutes to about 2 hours, about 30 minutes to about 2 hours, about 45 minute to about 90 minutes, or about one hour following exposure of the prosthesis to a fluid. In still other embodiments, the ability of the absorbent material of the cuff to absorb is delayed because the absorbent material itself or a material that is mixed in or otherwise substantially interspersed or integrated with the absorbent material is altered in response to one or more conditions (e.g., temperature, pH, and the like) that are present at the implantation site. For example, the absorbent material may include or may be provided along with a polymer that changes shape over time in response to exposure to the fluid or some other environmental cue present at the implantation site, and such shape change permits the initiation or the acceleration of the absorption of fluid by the absorbent material.

Exemplary substances that may be used to form the absorbent material include any crosslinked hydrogel component. A crosslinked hydrogel component may be based on covalent crosslinks, physical/ionic crosslinking, or both. Nonlimiting examples include poly(acrylic acid), poly(ethylene glycol), poly(ethylene oxide), poly(propylene oxide), poly(vinyl alcohol), polyvinyl pyrrolidinone, poly(hydroxy ethyl methacrylate), poly(amino acids), Dextran, polysaccharides, and proteins. Further examples of substances that may be used to form the absorbent material include sodium polyacrylate, polyacrylamide copolymer, ethylene maleic anhydride copolymer, carboxy-methyl-cellulose polyvinyl alcohol copolymers, polyethylene oxide, and polyacrylonitrile.

Any "super absorbent" material, for example, a super absorbent polymer, also may be used. As used herein, a "super absorbent" material is one that features an increase in volume swelling ratio (Qv; swollen volume divided by "dry" volume or volume before any fluid has been absorbed) from 1 to about 5-1000. Some examples of super absorbent materials are listed above. Those of ordinary skill in the art can readily identify other suitable materials that may be characterized as "super absorbent" and any such material may be used. Preferably, the cuff is configured so that expansion occurs predominantly in a single direction. For example, the expansion may predominantly in a direction that is substantially perpendicular relative to the outer surface of the stent. If the cuff comprises a continuous ring of absorbent material that forms a complete circle around the outer surface of the stent, the direction of expansion of the absorbent material may be characterized as radial. Because the stent in its expanded state will be sufficiently rigid to resist compression as a result of any radial expansion by the absorbent material in the direction towards the surface of the stent, the radial expansion of the absorbent material will be substantially unidirectional in the direction away from the surface of the stent, i.e., towards the interior surface of the mitral valve annulus. As described above, the expansion of the absorbent material creates a seal between the cuff and the mitral valve annulus that prevents perivalvular leakage.

A prosthesis according to the present disclosure may further comprise a webbing that is disposed at the upper flange, lower flange, or both. The webbing may comprise an absorbent material. The presence of the webbing may assist with the adhering (i.e., the affixing, anchoring, and/or sealing) of the prosthesis at the implantation site. Accordingly, the webbing may expand by absorption of a fluid, and the resulting adhering may be delayed for a time sufficient to permit positioning of the prosthesis at the implantation site. When one or both of the upper and lower flanges comprise discrete elements, such as individual stent elements as described above, a portion of the webbing may be disposed between at least one pair of the individual stent elements of either or both of the flanges. Preferably, the webbing is disposed between a plurality of pairs of individual stent elements of the upper anchoring flange and between a plurality of pairs of individual stent elements of the lower anchoring flange. When one or both of the upper and lower flanges comprise flaps, lobes, or other projections, part or all of each of the projections may be fitted with webbing. Each of the characteristics of the materials or components that are described above with respect to the cuff may be present in the webbing. Thus, the webbing the may comprise one or more materials, components, or both that creates a delay in the absorption of fluid or that provides a sufficiently slow rate of absorption of the fluid, such that the webbing does not expand to the degree required to adhere the prosthesis to the implantation site until the desired period of delay has elapsed.

The prostheses of the invention also comprise a valve comprising at least one leaflet that is fixedly attached to the interior surface of the stent. The attachment of the leaflet or leaflets to the interior surface of the stent need not be direct; for example, a valve support ring may be fixedly attached to the interior surface of the stent, and the valve(s) may be fixedly attached to the valve support ring. The valve may comprise one leaflet, two leaflet, or three leaflets. The leaflets are preferably derived from a biological source, such as mammalian pericardium. For example, the leaflets may be made from bovine, equine, ovine, caprine, or porcine pericardium. In other embodiments, the leaflets may be derived from animal valves, preferably mammalian valves. Nonlimiting examples include bovine jugular vein valves, porcine pulmonary valves, and porcine aortic valves. Those of ordinary skill in the art will appreciate how to select the appropriate valve for the desired purpose.

FIG. 1 provides three views of an exemplary prosthesis 2. Prosthesis 2 comprises a stent 4 having an upper anchoring flange 6 and a lower anchoring flange 8. As shown in FIGS. 1A and 1C, respectively, stent 4 has an expanded state and an unexpanded state. FIG. 1B provides a top perspective of exemplary prosthesis 2. Upper flange 6 and lower flange 8 comprise individual stent elements that are substantially coiled when stent 4 is in the expanded state (FIGS. 1A, 1B) and are substantially straightened when stent 4 is in the unexpanded state (FIG. 1C). As stent 4 is compressed and elongated, the stent elements also elongate and straighten to allow prosthesis 2 to fold and fit through a positioning catheter. Prosthesis 2 also comprises a cuff 10a, 10b that is disposed circumferentially around the outer surface of stent 4. As shown in FIG. 1C, before prosthesis 2 is positioned at the site of implantation, cuff 10a will not have expanded by absorption of fluid. However, as depicted in FIGS. 1A and 1B, once prosthesis 2 has been exposed to fluid and the desired amount of time has elapsed for positioning prosthesis 2 at the implantation site, cuff 10b will have absorbed fluid and expanded radially in the direction substantially away from the surface of stent 4 to substantially adhere prosthesis 2 at the implantation site. Prosthesis 2 also includes leaflets 12 that are fixedly attached to the interior surface of stent 4. The prosthesis depicted in FIG. 1 includes three leaflets, which can most clearly be ascertained in FIG. 1B.

In another aspect, there are disclosed methods for replacing a damaged or diseased mitral valve in a subject comprising: delivering to an implantation site of the subject a mitral valve prosthesis comprising a self-expanding stent comprising an outer surface, an interior surface, a middle region, an upper anchoring flange, and a lower anchoring flange, wherein the stent has an unexpanded and an expanded state; a cuff comprising an absorbent material disposed at least partially circumferentially around the outer surface of the stent and a valve comprising at least two leaflets fixedly attached to the interior surface of the stent; and expanding the cuff by absorption of a fluid to substantially adhere the prosthesis at an implantation site, wherein the adhering is delayed for a time sufficient to permit positioning of the prosthesis at the implantation site.

Each of the attributes, components, materials, and the like that are described above with respect to the inventive mitral valve prostheses may be used in accordance with the present methods.

Delivery of the mitral valve prosthesis to an implantation site may be accomplished transatrially, transapically, or percutaneously. Delivery of the prosthesis may be followed by one or more positioning steps (i.e., positioning and, if desired, repositioning), whereby the location of the prosthesis may be adjusted for optimal positioning in relation to the mitral valve annulus.

Figure 3:
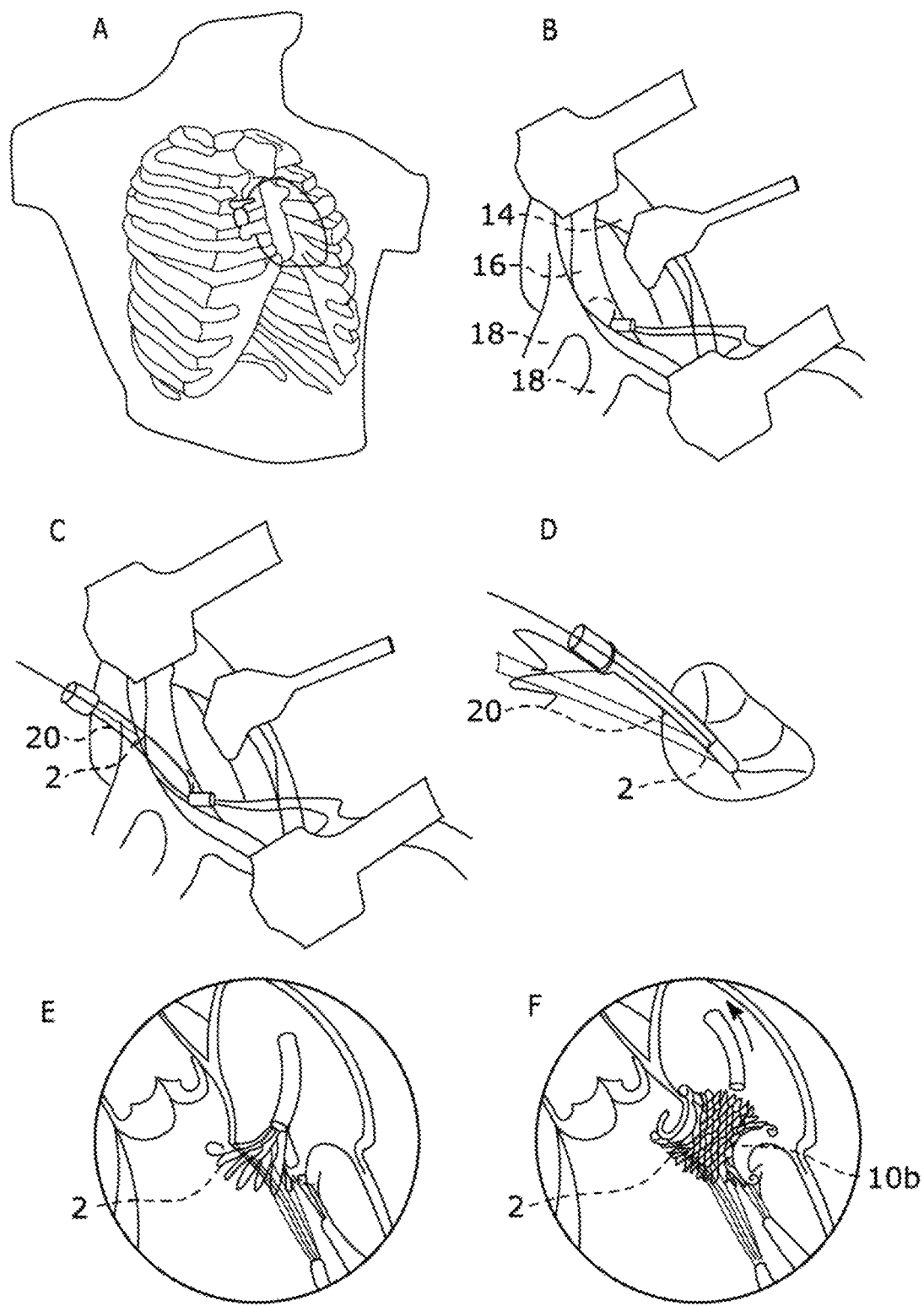
FIG. 3 illustrates steps from an exemplary procedure for transatrial delivery of a prosthesis according to the present disclosure.

For transatrial delivery, an exemplary procedure may be performed as follows and as illustrated in FIG. 3. A small (2-3 cm) thoracotomy through the inter costal space is made (FIG. 3A). The inter-atrial plane is developed. As shown in FIG. 3B, the right atrium 14 is retracted, and a purse string suture is placed in the left atrium 16. Right pulmonary veins are shown as item 18. Then, a steerable introducer catheter 20 is placed into the left atrium through the purse string (FIG. 3C). The catheter is advanced through the mitral valve annulus (FIG. 3D). Its position may be guided and confirmed by echocardiography. The prosthesis 2 is introduced through the catheter 20. The ventricular flange expands first and anchors to the ventricular side of the annulus and the subvalvular apparatus (leaflets, chordea, left ventricular wall) (FIG. 3E). The remainder of the stent and atrial flange are delivered, also under echocardiographic guidance (not shown). The atrial flange expands and anchors to the annulus and left atrium. The sealing cuff remains flaccid during the ensuing 60 minutes to allow documentation by echocardiography that the valve's position and function are adequate. After an hour in place the cuff 10b fully expands to seal the device against the native mitral valve annulus (FIG. 3F).

For transapical delivery, an exemplary procedure may be performed as follows. A small left thoracotomy is performed—similar in size to that which is used during the transatrial delivery procedure. A purse string suture is place in the left ventricular apex. A steerable catheter introducer is then placed into the left ventricle through the purse string. The introducer catheter 20 is guided through the mitral valve annulus into the left atrium under echocardiographic guidance. For this approach, the device may be designed so that the atrial flange is deployed and positioned first. The sealing technology by means of the cuff and optional webbing may be similar to that described above with respect to the exemplary transatrial delivery process.

Percutaneous delivery may be venous or arterial. When percutaneous delivery is the intended procedure, the prosthesis is configured accordingly, e.g., foldable enough to be placed via peripheral venous or arterial access.

Figure 4:
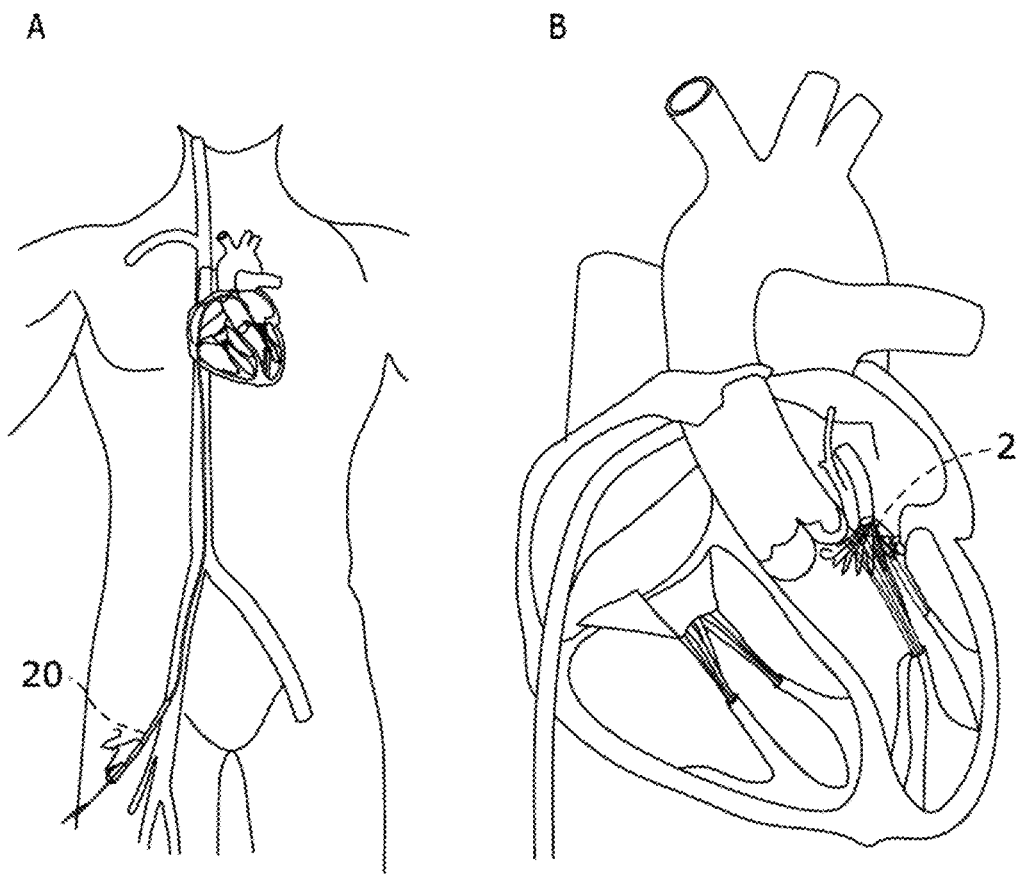
FIG. 4 depicts steps from an exemplary procedure for venous percutaneous delivery of a prosthesis according to the present disclosure.

Venous percutaneous delivery may be performed as follows and as illustrated in FIG. 4. Access to the femoral vein is achieved by standard techniques that will be readily appreciated by those skilled in the art. A steerable catheter 20 is then introduced into the venous system and guided to the right atrium using fluoroscopic guidance (FIG. 4A). Once in the right atrium, standard techniques are used to traverse the catheter across the intra-atrial septum to the left atrium (FIG. 4B). The prosthesis 2 is then deployed under echocardiographic guidance as described in the transatrial approach.

For aterial percutaneous delivery, an exemplary procedure may be performed as follows. Access to the femoral artery is achieved by standard techniques. A steerable catheter is then introduced into the arterial system and guided to the aortic root and into the left ventricle using fluoroscopic guidance. Once in the left ventricle the device is deployed as described above in connection the transapical approach.

General Embodiment II

The following description pertains to a second general embodiment of the present disclosure, which pertains to inventive valve prostheses; methods for replacing a damaged or diseased valve; systems for delivering a valve prosthesis; kits; and, methods for delivering a valve prosthesis.

In one aspect, provided are valve prostheses comprising an at least partially self-expanding stent comprising a wire framework defining outer and interior surfaces, and upper and lower anchoring flanges interposed by a middle region, the stent having an unexpanded and an expanded state, and the lower anchoring flange having at least one geometric dimension that is greater than the corresponding dimension of the upper anchoring flange; and a valve comprising at least one leaflet fixedly attached to the interior surface of the stent.

The stent may be configured to be at least partially self-expanding. For example, the stent may be capable of self-expanding to its state of maximal expansion, or, to at least some degree, the stent may be configured such that it must be forcibly expanded, for example, by a balloon. For example, the stent may be configured so that 100% of its requisite expansion occurs without any contribution by a mechanism other than the stent itself, or may be configured so that 99% or less, but more than 0%, of the requisite expansion occurs without any contribution by a mechanism other than the stent itself. In certain embodiments, the stent is fully self-expanding.

The at least partially self-expanding stent may comprise a shape-memory or "superelastic" material exhibiting large elastic strains. An exemplary material is nitinol, a nickel-titanium alloy. In one embodiment, the stent comprises a nitinol wire weave. Any other material possessing similar characteristics may also be used in the construction of the self-expanding stent, and more generally, and suitable, biocompatible material may be used to form the stent, whether it is self-expanding or not. Exemplary materials include stainless steel, cobalt/chromium alloy, cobalt/chromium/nickel alloy, nickel/chromium alloy, platinum, platinum/iridium alloy, among others. The stent may comprise one or more other materials that are themselves not self-expanding but that do not inhibit or otherwise interfere with the ability of the stent to self-expand. For example, any biocompatible material may be included to add any other desired structural feature to the stent. Exemplary biocompatible materials include stainless steel, tantalum, platinum alloys, niobium alloys, and cobalt alloys, among others. Additionally or alternatively, one or more bioabsorbable materials may be used in forming the stent. Part or all of the stent may be coated with a composition comprising a drug, so that the stent is capable of eluting drug in situ.

The stent comprises a wire framework that is formed from the material that allows the stent to be at least partially self-expanding, in addition to any other compatible materials as described above. The framework can be formed from wire using conventional techniques, such as coiling, weaving, braiding, or knitting. In a preferred embodiment, the stent comprises a wire weave. In certain embodiments, the wire framework may be welded or otherwise joined at some or all crossover points, thereby forming a structure that, at least in some places, is not hinged. The formation of wire frameworks is readily appreciated among those skilled in the art and the present disclosure is intended to embrace any suitable technique, including any functionally acceptable framework geometry.

The present inventors have found that the amount of radial force that is exerted by a stent can be an important determinant both of how well the stent will be anchored to the site of implantation and of the quality of the seal that is formed between the stent and the site of implantation, e.g., between the stent and the inner walls of a valve annulus. Pursuant to the present invention, it has been discovered that at least three factors contribute to the outward radial force that the stent exerts. First, the thickness of the wire that is used to form the framework influences the degree of radial force that the stent exerts. In accordance with the present disclosure, the thickness of the wire that is used to form the framework may be about 0.005 inches to about 0.030 inches. For example, the wire may have a thickness of about 0.010 inches, about 0.015 inches, about 0.020 inches, about 0.025 inches, or about 0.030 inches. It has also been discovered that the density of the wire framework affects the radial force that is exerted by the stent. The parameters that can be used to describe the density of the wire framework are defined more fully infra. Third, the radial force that is exerted by the stent is influenced by the diameter of the stent in the expanded state relative to the diameter of the major dimension of the valve annulus into which the stent is to be implanted. Valve annuli may be roughly circular, but in many instances are substantially elliptical or saddle-shaped, such that the annulus will have a major and a minor dimension (diameter). In the case of a circular annulus, the "major dimension" will simply be the diameter of the annulus. It has presently been discovered that the stent exerts a beneficial amount of radial force when the diameter of the stent in its expanded state is about 95% to about 125% of the major dimension of the valve annulus. For example, an expanded stent having a diameter that is about 95%, about 100%, about 105%, about 110%, about 115%, about 120%, or about 125% of the major dimension of the valve annulus will be conducive to the exertion of a beneficial amount of radial force. Stated, in absolute terms, this can mean that an expanded stent may have a diameter of about 25 to about 50 mm.

The stent comprises a middle region having various dimensions, including an unexpanded length, an unexpanded diameter, an expanded length, and an expanded diameter. The unexpanded length is preferably substantially the same as or greater than the expanded length, and the expanded diameter is greater than the unexpanded diameter. The unexpanded diameter may be any size that enables the unexpanded stent to be translated through a subject's vasculature during delivery. For example, the unexpanded diameter may be of a size that enables the unexpanded stent to fit within the interior of a catheter (or a related component, such as a compression sleeve, which is more fully described herein) having a diameter of about 1 mm to about 13 mm, preferably about 1 mm to about 8 mm. The expanded length may substantially correspond to the length that is about the same as or longer than that of the annulus between two chambers of a human subject's heart, or between one chamber and the associated artery, such as the left ventricle and the aortic artery. Preferably, the expanded length of the stent is longer than that of such an annulus. Because the length of a valve annulus, such as the mitral valve annulus, may vary from subject to subject, a particular subject may be matched with a stent having an expanded length that is appropriate for the valve annulus of that subject. In general, the expanded length may be about 0.5 cm to about 5 cm, about 1 cm to about 4 cm, about 1.5 cm to about 3.5 cm, or about 2 cm to about 3 cm. As described above, the expanded diameter may be about 95% to about 125% of the major dimension of the subject's valve annulus. Even in embodiments wherein the present prosthesis further comprises a cuff comprising an absorbent material that is disposed at least partially circumferentially around the outer surface of the stent, which is discussed more fully herein, the expanded diameter preferably falls within the range recited above relative to the major dimension of the subject's valve annulus.

The prostheses according to the present disclosure may be configured to be delivered transatrially, transapically, or percutaneously. Thus, the dimensions of the prosthesis, the type of material used for the stent, cuff, or other components, the presence or absence of a drug coating on the stent, the type of flanges that are included, the framework pattern (e.g., weave) of the stent, the length of delay of absorption of fluid, and other factors may all be manipulated in order to configure the prosthesis for transatrial, transapical, or percutaneous delivery, as desired. Those skilled in the art will readily appreciate the characteristics that are required for delivery of a stented device by the transatrial, transapical, or percutaneous route, respectively, and may select accordingly from the wide range of characteristics described herein.

In addition to the middle region the self-expanding stent comprises an upper flange and a lower flange. In the most simple embodiment, one or both of the flanges comprise the longitudinal ends or margins of the middle region. For example, one or both of the flanges may be a "lip" of stent material that extends partly or fully around the circumference of the stent at a longitudinal end of the middle region. In other embodiments, one or both of the flanges may be configured to provide an anchoring functionality that substantially affixes the stent at the location of the valve annulus. For example, the lower flange may be configured to anchor to the ventricular side of a mitral annulus, and the upper flange may be configured to anchor to the atrial side of the mitral annulus. The respective configurations of the upper and lower flange may, but need not be, the same; thus, the lower flange may adopt a different configuration than the upper flange. The upper flange, lower flange, or both may comprise a plurality of protruding stent elements. Any flange design, whether consisting of a unitary structure or numerous discrete elements, is contemplated for purposes of the present disclosure. For example, the flanges may comprise a plurality of protruding stent elements that respectively comprise individual wires or bundled sets of wires. The plurality of wires may comprise a regularly or irregularly spaced array, and the wires themselves may be present as single strands, or as grouped or bundled sets of two, three, four, or more wire strands. In other embodiments, the flanges may comprise a plurality of wire loops. The wire loops may be integral with the wire framework of the stent. For example, the stent may comprise wire weave that defines (in addition to the other elements of the stent) flanges that comprise a plurality of wire loops. The wire loops may comprise a regularly or irregularly spaced array.

Each flange may have a configuration that corresponds to the unexpanded state of the stent, and a configuration that corresponds to the expanded state of the stent. For example, when one or both of the flanges comprise a plurality of individual stent wires, the elements may be substantially straightened when the stent is in the unexpanded state and may be substantially coiled when the stent is in the unexpanded state. In other instances, a flange may comprise one or more elements that define flaps, lobes, loops, or other projections that may be oriented substantially parallel with the long axis of the stent when the stent is in an unexpanded state and are differently oriented when the stent is in an expanded state. Some embodiments are such that the upper flange and lower flange each comprise a plurality of protruding stent elements that are each substantially straightened when the stent is in the unexpanded state and are each substantially bent back towards the middle region of the stent when the stent is in the expanded state.

It has presently been discovered that a stent that comprises a lower anchoring flange having at least one geometric dimension that is greater than the corresponding dimension of the upper anchoring flange is capable of reliably adhering the prosthesis to the site of implantation. Traditionally, replacement of damaged or diseased valves consisted of the removal of the defunct valve tissue in order to clear a space for the prosthetic valve apparatus and avoid unwanted interference with the functioning of the prosthesis. The present design does not require the removal of defunct valve tissue, and in fact benefits from the presence of such tissue, because it is capable of grasping the tissue that is present at the site of implantation (whether such tissue comprises defunct valve material or otherwise) by virtue of the lower anchoring flange, and is capable of similar grasping, as well as "capping", by virtue of the upper anchoring flange. For example, when the site of implantation is the mitral valve annulus, the inventive prosthesis securely adheres to the site of implantation because, inter alia, of the action of lower anchoring flange to grasp the defunct valve tissue and annulus tissue on the ventricular side, and of the action of the upper anchoring flange to grasp such tissue and likewise provide a "cap" on the atrial side of the annulus.

As used herein, the terms "lower" and "upper" are merely terms of convenience; a prosthesis for implantation in a mitral valve annulus, for example, will be positioned in situ such that the "lower" anchoring flange is oriented on the ventricular side of the annulus and thereby substantially "downwards", and the convention therefore arose to use the term "lower" to designate the ventricular-side flange, which possesses a geometric dimension that is greater than the corresponding dimension on the upper flange. In general, because the use of the terms "upper" and "lower" are merely conventions, there is no requirement for the "lower" anchoring flange to be oriented substantially or even partially "downwards" when the prosthesis is used in other contexts.

The geometric dimension that is greater in the lower anchoring flange as compared with the upper anchoring flange may be any dimension that is shared by the respective flanges. Thus, the geometric dimension may be length, width, height, or any other parameter. In one example, the lower anchoring flange comprises a plurality of protruding stent elements of equal length, wherein the protruding stent elements of the lower anchoring flange are longer than a series of protruding stent elements that form the upper anchoring flange. When the upper and lower anchoring flange respectively comprise a plurality of protruding stent elements, the lower anchoring flange may be said to have a geometric dimension that is greater than the corresponding dimension of the upper anchoring flange when more than 50%, more than 60%, more than 70%, more than 75%, more than 80%, more than 85%, more than 90%, more than 95%, or 100% of the protruding stent elements of the lower flange have a greater dimension than the protruding stent elements of the upper flange.

Figure 5:
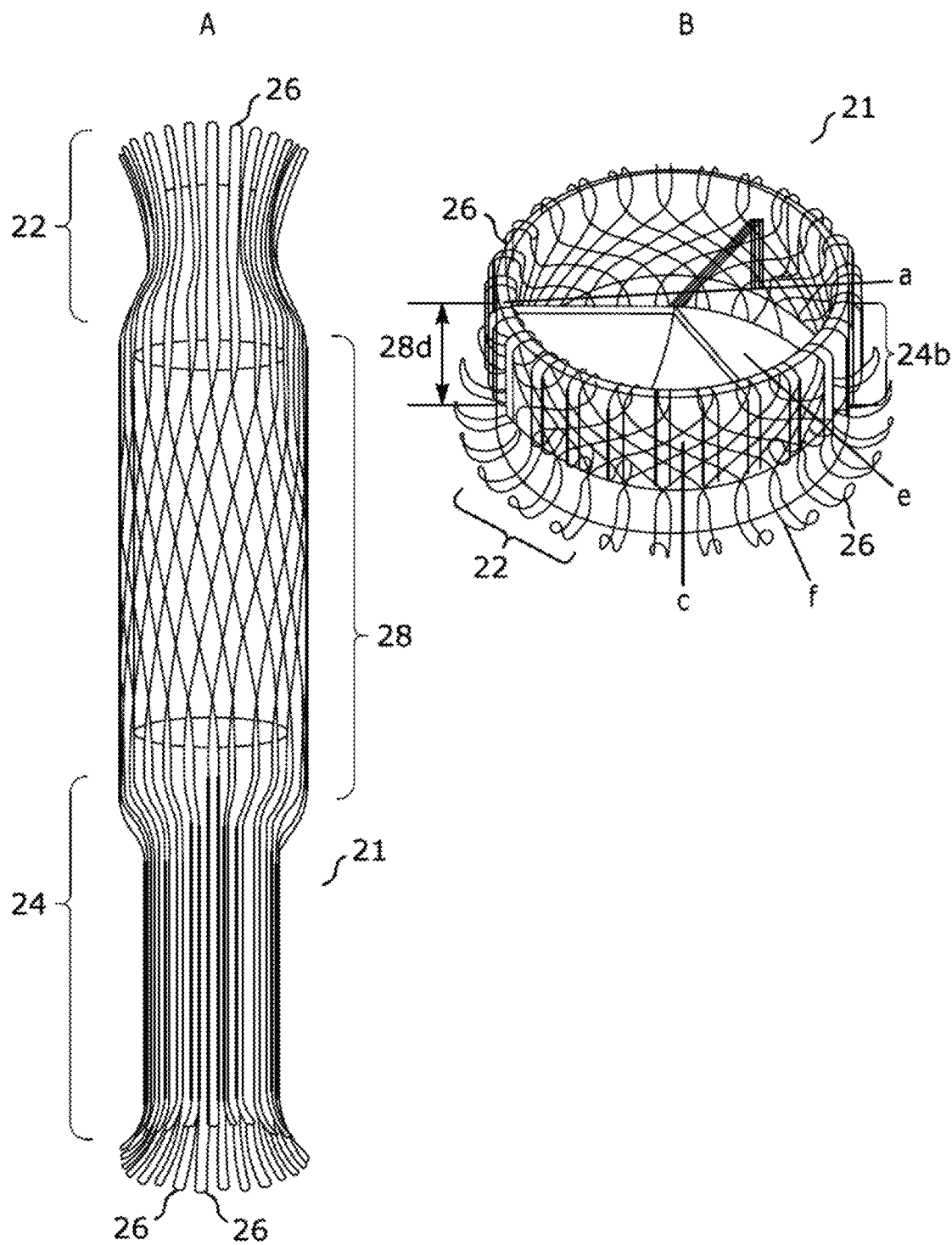
FIG. 5 provides views of an exemplary stent for use in a prosthesis according to the present invention.

FIG. 5 provides views of an exemplary stent 21 of this variety, having an upper flange 22 and a lower flange 24 of which each comprises a plurality of protruding stent elements 26. Protruding stent elements 26 are substantially straightened and oriented substantially parallel with the long axis Y when stent 21 is in an unexpanded state (FIG. 5A) and that are substantially bent back towards the middle region 28 when stent 21 is in the expanded state (FIG. 5B). The stent 21 of FIG. 5B is vertically inverted relative to that of FIG. 5A, i.e., the upper flange 22 in FIG. 5B appears at the bottom of the drawing of stent 21, rather than at the top portion (as in FIG. 5A). The protruding stent elements 26 of the lower flange 24 are longer than the protruding stent elements 26 of the upper flange 22. When the stent 21 is in an expanded state, the protruding stent elements 26 exert a force in the direction of the stent body, such that any material that is interposed between a protruding element 26 and the outer surface of the middle region of the stent 28 will be trapped between the two elements. Accordingly, when a prosthesis comprising a stent such as that described herein is delivered to an implantation site and shifts from its unexpanded state to its expanded state, loose tissue at the implantation site, such as defunct valve tissue, will be ensnared between the respective flanges and the middle region of the stent. This action significantly contributes to the anchoring of the prosthesis to the site of implantation. Example 2, below, discloses the measurement of the force that was required to extract an exemplary valve prosthesis according to the present disclosure from a site at which the prosethesis had been implanted.

FIG. 5B denotes various dimensions of exemplary stent 21 in its expanded state. Line a designates the diameter of stent 21; line b indicates the length of the individual protruding stent elements 26 of the lower flange 24; line c designates the height of stent 21, including the contribution of the upper and lower flange elements 22, 24; line d refers to the height of middle region 28; line e) points to the diameter of the lower flange elements 24 that are bent back towards middle region 28; and, line f) designates the diameter of the upper flange elements 22 that are bent back towards middle region 28.

The diameter of the stent in its expanded state may be, for example, about 25 to about 55 mm. The length of an individual protruding stent element of a lower flange may be, for example, about 5 to about 45 mm. The height of the stent in its expanded state (i.e., the dimension running parallel to the stent lumen—designated by line c in FIG. 5B), including the contribution of the upper and lower flange elements, may be, for example, from about 15 to about 55 mm. The height of the middle region alone when the stent is in its expanded state may be, for example, about 15 to 45 mm. The diameter of the lower flange elements that are bent back towards the middle region (as designated by line e in FIG. 5B) may be, for example, about 1 to about 8 mm. The diameter of the upper flange elements that are bent back towards the middle region of the stent (as designated by line f in FIG. 5B) may be, for example, about 3 to about 12 mm.

With respect to the compressed stent shown in FIG. 5A, the total length of the stent may be from about 4 to about 15 cm, and the width of the compressed stent at the middle region 28 may be about 5 to about 15 mm, preferably about 6 to about 12 mm.

Figure 6:
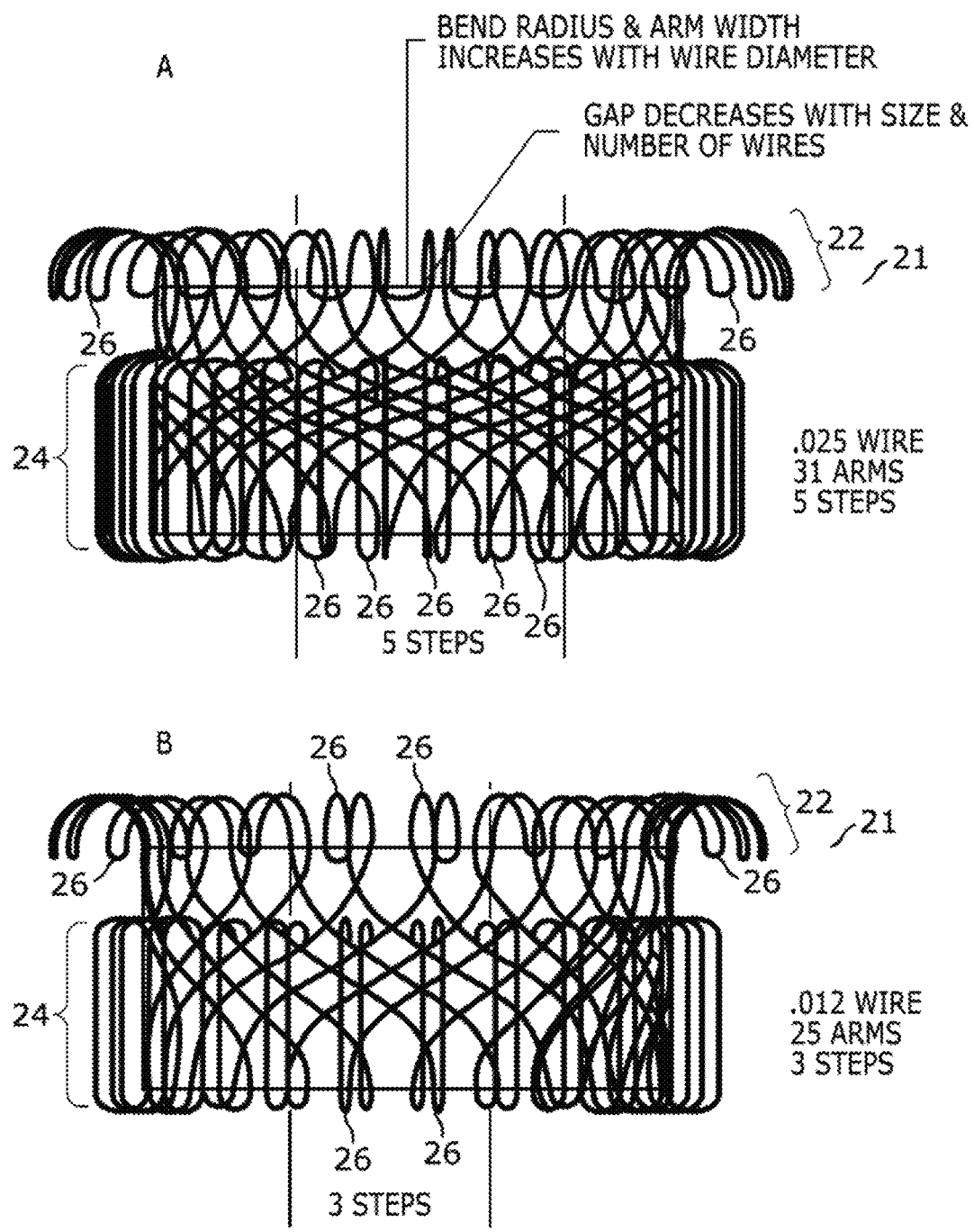
FIG. 6 provides an illustrative example of how to characterize wire weave density, as well as how wire weave density and wire thickness respectively affect various parameters of the inventive stent.

As indicated above, the amount of outward radial force that is exerted by the stent is influenced by, inter alia, the density of the wire framework. In general, a higher density results in the exertion of a greater outward radial force. FIG. 6 provides an illustrative example of how to characterize wire weave density, as well as how wire weave density and wire thickness respectively affect various parameters of the inventive stent 21. The process of constructing a wire weave may described in terms of "steps" and "step-overs".

FIG. 6A shows one embodiment of an inventive stent 21 comprising wire weave that includes an upper flange 22 comprising thirty-one individual protruding stent elements and a lower flange 24 comprising thirty-one individual protruding stent elements. With respect to the embodiment shown in FIG. 6A, each individual protruding stent element 26 constitutes a "step" in the construction process, and each "step" requires 5 "step-overs" to form the body of the stent 21.

FIG. 6B shows a further embodiment of an inventive stent 21 comprising wire weave that includes an upper flange 22 comprising twenty-five individual protruding stent elements and a lower flange 24 comprising twenty-five individual protruding stent elements. For the embodiment of FIG. 6B, each individual protruding stent element 26 constitutes a "step" in the construction process, and each "step" requires 3 "step-overs" to form the body of the stent 21.

The number of "step-overs" that may be used to form a stent comprising wire weave according to the present invention can be 2, 3, 4, 5, 6, 7, 8, 9, or 10.

FIGS. 6A and 6B also illustrate how the thickness of the wire that is used to form a stent 21 comprising wire weave can influence certain characteristics of the stent. The embodiment of FIG. 6A involves the use of wire having a thickness of 0.025 inches, whereas the embodiment of FIG. 6B involves the use of wire having a thickness of 0.012 inches. The terminal bend of each individual protruding stent element 26 is wider in the case of the embodiment of FIG. 6A as compared with the corresponding elements of FIG. 6B, because thicker wire is used in the case of the former than in the latter. As indicated previously, the thickness of the wire that is used to form the framework of an inventive stent may be about 0.005 inches to about 0.030 inches.

The present valve prostheses may also comprise a cuff comprising an absorbent material that is disposed at least partially circumferentially around the outer surface of the stent. The term "cuff" is intended to embrace a continuous ring of absorbent material that forms a complete circle around the outer surface of the stent; any other conformation that involves a contiguous portion of absorbent material, such as a strip that forms a spiral around the outer surface of the stent; one, two, three or more disparate patches or strips (or any other shape or configuration) of absorbent material disposed on the outer surface of the stent; or, any combination of one or more contiguous portions of material and disparate patches, strips, and the like. In a preferred embodiment, the cuff comprises a continuous ring of absorbent material that forms a complete circle around the outer surface of the stent.

When present, the cuff comprises an absorbent material that expands by absorption of a fluid to substantially adhere the prosthesis at the implantation site. When the disclosed prostheses are used to replace a damaged or nonfunctional mitral valve, the implantation site is the mitral valve annulus. As used herein to "adhere" may mean to substantially affix or anchor the prosthesis at the implantation site, to create a seal between the cuff and the mitral valve annulus that is substantially impermeable to fluid, or both. It has been presently discovered that the cuff can form a seal that reliably prevents perivalvular leakage between the atrium and ventricle, such that when the prosthesis is in place, the only fluid that passes between the atrium and ventricle is that which is allowed to pass by the activity of the replacement valve itself.

In embodiments that include a cuff, the adhering of the prosthesis is delayed for a time sufficient to permit positioning of the prosthesis at the implantation site. For example, because the procedure for positioning the prosthesis via a catheter at the implantation site may last 40 minutes, the expansion by the cuff by absorption of fluid to a sufficient degree such as to adhere the prosthesis to the implantation may be delayed until that time has elapsed. Thus, the cuff comprises one or more materials, components, or both that creates a delay in the absorption of fluid or that provides a sufficiently slow rate of absorption of the fluid, such that the cuff does not expand to the degree required to adhere the prosthesis to the implantation site until the desired period of delay has elapsed. The period of delay may be measured starting at the point in time where the prosthesis is exposed to a fluid (e.g., blood). The delay period may be about 1 minute, about 2 minutes, about 5 minutes, about 7 minutes, about 10 minutes, about 15 minutes, about 20 minutes, about 30 minutes, about 45 minutes, about 1 hour, about 75 minutes, about 90 minutes, or about 2 hours. The type of cuff that is selected for use with the prosthesis may depend on the difficulty of the procedure to deliver the prosthesis to the implantation site.

The absorbent material of the cuff may itself absorb fluid at a sufficiently slow rate to delay the adhering of the prosthesis at the implantation site. In other embodiments, the absorbent material of the cuff may feature a variable rate of absorption, such that the rate of absorption is low for an initial period of time but that increases over time or after a period of time. For example, the absorbent material may have a fluid absorption rate of about 0 µL to about 20 µL per minute for a first period of time following exposure of the prosthesis to the fluid, and a fluid absorption rate from about 10 to about 200 µL per minute after the first period of time. The period of time after which the rate of absorption increases may be about 10 minutes, about 15 minutes, about 20 minutes, about 30 minutes, about 45 minutes, about 1 hour, about 90 minutes, about 2 hours, about 180 minutes, or about 2 hours. In other embodiments, the ability of the absorbent material of the cuff to absorb fluid is delayed. For example, the absorbent material of the cuff may be completely or partially covered with or contained within a material that affects the ability of the absorbent material to absorb fluid. The absorbent material may be completely or partially covered with or contained within a cover material, e.g., a film or fabric, that is permanently impermeable to fluid, but that is removable and is removed when the desired period of delay has elapsed; the removal of the cover material may be effected while the prosthesis is in situ at the implantation site, for example, by using a catheter-based removal tool to grasp and remove the cover material. Any material that is substantially impermeable to fluid (such as water, blood, and the like) and that is biocompatible may be used to form the cover material. Nonlimiting examples include polyurethanes, polyethylenes, polydimethylsiloxane, silicones, rubbers, and polyvinyl chloride. In other embodiments, the absorbent material may be completely or partially covered with or contained within a cover material, e.g., a film or fabric, that is temporarily impermeable to fluid, but that becomes permeable to fluid after a desired period of delay. For example, the cover material may be degradable over time, or may comprise a material that degrades or is altered in response to a change in temperature, pH, or some other environmental cue that is present at the implantation site. In other embodiments, the absorbent material may be completely or partially covered with or contained within a cover material that is permeable to fluid, but the transfer of fluid across such cover material and/or saturation of by the cover material by fluid is sufficiently slow to provide a delay before the absorbent material absorbs a sufficient amount of fluid to adhere to the implantation site. The period of delay that is provided by a cover material may be, for example, about 5 minutes to about 3 hours, about 10 minutes to about 3 hours, about 20 minutes to about 2 hours, about 30 minutes to about 2 hours, about 45 minute to about 90 minutes, or about one hour following exposure of the prosthesis to a fluid. In still other embodiments, the ability of the absorbent material of the cuff to absorb is delayed because the absorbent material itself or a material that is mixed in or otherwise substantially interspersed or integrated with the absorbent material is altered in response to one or more conditions (e.g., temperature, pH, and the like) that are present at the implantation site. For example, the absorbent material may include or may be provided along with a polymer that changes shape over time in response to exposure to the fluid or some other environmental cue present at the implantation site, and such shape change permits the initiation or the acceleration of the absorption of fluid by the absorbent material.

Exemplary substances that may be used to form the absorbent material include any crosslinked hydrogel component. A crosslinked hydrogel component may be based on covalent crosslinks, physical/ionic crosslinking, or both. Nonlimiting examples include poly(acrylic acid), poly(ethylene glycol), poly(ethylene oxide), poly(propylene oxide), poly(vinyl alcohol), polyvinyl pyrrolidinone, poly(hydroxy ethyl methacrylate), poly(amino acids), Dextran, polysaccharides, and proteins. Further examples of substances that may be used to form the absorbent material include sodium polyacrylate, polyacrylamide copolymer, ethylene maleic anhydride copolymer, carboxy-methyl-cellulose polyvinyl alcohol copolymers, polyethylene oxide, and polyacrylonitrile.

Any "super absorbent" material, for example, a super absorbent polymer, also may be used in the cuff, when present. As used herein, a "super absorbent" material is one that features an increase in volume swelling ratio (Qv; swollen volume divided by "dry" volume or volume before any fluid has been absorbed) from 1 to about 5-1000. Some examples of super absorbent materials are listed above. Those of ordinary skill in the art can readily identify other suitable materials that may be characterized as "super absorbent" and any such material may be used. Preferably, the cuff is configured so that expansion occurs predominantly in a single direction. For example, the expansion may predominantly in a direction that is substantially perpendicular relative to the outer surface of the stent. If the cuff comprises a continuous ring of absorbent material that forms a complete circle around the outer surface of the stent, the direction of expansion of the absorbent material may be characterized as radial. Because the stent in its expanded state will be sufficiently rigid to resist compression as a result of any radial expansion by the absorbent material in the direction towards the surface of the stent, the radial expansion of the absorbent material will be substantially unidirectional in the direction away from the surface of the stent, i.e., towards the interior surface of the mitral valve annulus. As described above, the expansion of the absorbent material can enhance the seal between the cuff and the valve annulus that prevents perivalvular leakage.

A prosthesis according to the present disclosure may further comprise a webbing that is disposed at the upper flange, lower flange, or both. The webbing may comprise an absorbent material. The presence of the webbing may assist with the adhering (i.e., the affixing, anchoring, and/or sealing) of the prosthesis at the implantation site. Accordingly, the webbing may expand by absorption of a fluid, and the resulting adhering may be delayed for a time sufficient to permit positioning of the prosthesis at the implantation site. When one or both of the upper and lower flanges comprise discrete elements, such as protruding stent elements as described above, a portion of the webbing may be disposed between at least one pair of the protruding stent elements of either or both of the flanges. Preferably, the webbing is disposed between a plurality of pairs of protruding stent elements of the upper anchoring flange and between a plurality of pairs of protruding stent elements of the lower anchoring flange. When one or both of the upper and lower flanges comprise flaps, lobes, loops, or other projections, part or all of each of the projections may be fitted with webbing. Each of the characteristics of the materials or components that are described above with respect to the cuff may be present in the webbing. Thus, the webbing the may comprise one or more materials, components, or both that creates a delay in the absorption of fluid or that provides a sufficiently slow rate of absorption of the fluid, such that the webbing does not expand to the degree required to adhere the prosthesis to the implantation site until the desired period of delay has elapsed.

The prostheses of the invention also comprise a valve comprising at least one leaflet that is fixedly attached to the interior surface of the stent. The attachment of the leaflet or leaflets to the interior surface of the stent need not be direct; for example, a valve support ring may be fixedly attached to the interior surface of the stent, and the valve(s) may be fixedly attached to the valve support ring. The valve may comprise one leaflet, two leaflet, or three leaflets. The leaflets are preferably derived from a biological source, such as mammalian pericardium. For example, the leaflets may be made from bovine, equine, ovine, caprine, or porcine pericardium. In other embodiments, the leaflets may be derived from animal valves, preferably mammalian valves. Nonlimiting examples include bovine jugular vein valves, porcine pulmonary valves, and porcine aortic valves. Those of ordinary skill in the art will appreciate how to select the appropriate valve for the desired purpose. For example, it will be recognized that the suitability of a particular type of valve and number of leaflets may be affected by the intended use of the valve prosthesis. In one instance, the intended use of the valve prosthesis may be the replacement of a damaged or diseased mitral valve, in which case it would be appreciated that a three-leaflet valve should be selected. The instant prostheses may be configured for replacing any cardiac valve, such as the pulmonary valve, the tricuspid valve, the aortic valve, or the mitral valve.

The present disclosure also includes methods for replacing a damaged or diseased valve in a subject comprising: delivering to an implantation site of the subject a valve prosthesis comprising an at least partially self-expanding stent comprising a wire framework definingouter and interior surfaces, and upper and lower anchoring flanges interposed by a middle region, the stent having an unexpanded and an expanded state, and the lower anchoring flange having at least one geometric dimension that is greater than the corresponding dimension of the upper anchoring flange; and a valve comprising at least one leaflet fixedly attached to the interior surface of the stent; and expanding the stent to substantially adhere the prosthesis at the implantation site.

Each of the attributes, components, materials, and the like that are described above with respect to the inventive valve prostheses may be used in accordance with the present methods.

Delivery of the valve prosthesis to an implantation site may be accomplished transatrially, transapically, or percutaneously. Delivery of the prosthesis may be followed by one or more positioning steps (i.e., positioning and, if desired, repositioning), whereby the location of the prosthesis may be adjusted for optimal positioning in relation to the valve annulus.

For transatrial delivery, an exemplary procedure may be performed as follows. A small (2-3 cm) thoracotomy through the inter costal space is made. The inter-atrial plane is developed. The right atrium is retracted, and a purse string suture is placed in the left atrium. Then, a steerable introducer catheter is placed into the left atrium through the purse string. The catheter is advanced through the mitral valve annulus. Its position may be guided and confirmed by echocardiography. The prosthesis is introduced through the catheter. The lower (ventricular) flange expands first and anchors to the ventricular side of the annulus and the subvalvular apparatus (leaflets, chordea, left ventricular wall). The remainder of the stent and upper (atrial) flange are delivered, also under echocardiographic guidance. The atrial flange expands and anchors to the annulus and left atrium. In embodiments of the prosthesis that include a cuff, the sealing cuff remains flaccid during the ensuing 60 minutes to allow documentation by echocardiography that the valve's position and function are adequate. After an hour in place the cuff fully expands to seal the device against the native mitral valve annulus.

For transapical delivery, an exemplary procedure may be performed as follows. A small left thoracotomy is performed—similar in size to that which is used during the transatrial delivery procedure. A purse string suture is place in the left ventricular apex. A steerable catheter introducer is then placed into the left ventricle through the purse string. The introducer catheter is guided through the mitral valve annulus into the left atrium under echocardiographic guidance. For this approach, the device may be designed so that the atrial flange is deployed and positioned first. The optional cuff and/or webbing may be similar to that described above with respect to the exemplary transatrial delivery process.

Percutaneous delivery may be venous or arterial. When percutaneous delivery is the intended procedure, the prosthesis is configured accordingly, e.g., foldable enough to be placed via peripheral venous or arterial access.

Venous percutaneous delivery may be performed as follows. Access to the femoral vein is achieved by standard techniques that will be readily appreciated by those skilled in the art. A steerable catheter is then introduced into the venous system and guided to the right atrium using fluoroscopic guidance. Once in the right atrium, standard techniques are used to traverse the catheter across the intra-atrial septum to the left atrium. The prosthesis is then deployed under echocardiographic guidance as described in the transatrial approach.

For aterial percutaneous delivery, an exemplary procedure may be performed as follows. Access to the femoral artery is achieved by standard techniques. A steerable catheter is then introduced into the arterial system and guided to the aortic root and into the left ventricle using fluoroscopic guidance. Once in the left ventricle the device is deployed as described above in connection the transapical approach.

In another aspect, provided are systems for delivering a valve prosthesis comprising an at least partially self-expanding stent to an implantation site comprising: a catheter comprising a distal end and a proximal end, a guidewire lumen to permit the catheter to be translated along a guidewire, a steering lumen for accommodating a tension cable for steering the catheter, and a dock at the distal end onto which the stent may be loaded. The present systems also comprise a retractable compression sleeve for compressing at least a portion of the stent while the stent is loaded onto the dock; a leading tip positioned distal to the dock for leading the catheter during delivery; and, a steering mechanism operably associated with the tension cable for deflecting the leading tip in at least one directional plane.

Unlike existing delivery systems, the disclosed systems are capable of housing, transporting, and delivering stents of valve prostheses according to the present disclosure, as well as stents of other configurations, including conventional stented devices. As will be discussed more fully herein, the present systems include a number of features that address certain challenges that are associated with the manipulation and implantation of at least partially self-expanding stents, including those having the characteristics of the stents that are used with the presently disclosed prostheses.

The catheter of the present system includes a distal end, which is the end of the catheter that is first introduced into the physiological point of entry during the stent implantation procedure. The proximal end of the catheter (defined herein as the end of the catheter that is closest to the operator of the system during use) remains outside of the subject. The instant catheters may have a length of about 20 cm to about 200 cm from the distal end to the proximal end. The outer diameter of the catheter may be about 0.5 cm to about 1.5 cm.

The catheter may be constructed from any suitable material, wherein suitability is determined by such considerations as biological compatibility, durability, the appropriate balance between rigidity and flexibility, and other readily appreciable factors based on the intended use of the catheter. For example, polyimide, polyethylene, polypropylene, Kalrez®, Simriz®, Viton®, Chemraz®, silicone, neoprene, nitrile, metal or metal alloys (such as Ti—Nb—Zr; see, e.g., U.S. Pat. No. 5,685,306) or any other combination thereof may be used. The materials used for the construction of the catheter, as well as the methods for the construction thereof, are readily appreciated by those skilled in the art, and all appropriate materials and means of construction are contemplated herein.

The catheter includes at least two lumens, the first being a guidewire lumen to permit the catheter to be translated along a guidewire, the second being a steering lumen for accommodating a tension cable for steering the catheter. The guidewire lumen is appropriately sized, shaped, and located within the catheter to accommodate a guidewire, such that the catheter may be translated over a guidewire that has been placed along the appropriate physiological pathway to a site of interest within a subject. The steering lumen is appropriately sized, shaped, and located within the catheter to accommodate a tension cable. The manipulation of a tension cable that is located within a lumen of the present catheters causes the deflection of the catheter, which in turn allows the catheter to be moved from a first location to a second location in situ. The selection and use of guidewires and steering tension cables are well known among those skilled in the art. There are no limitations on the relative arrangement of the lumens within the catheter. However, it is traditional for a guidewire lumen to be located towards the center of a catheter. In one embodiment, the guidewire lumen and the steering lumen are provided in a side-by-side arrangement within the catheter. In other instances, the guidewire lumen may be located substantially in the center of the catheter, and the steering lumen is located between the guidewire lumen and the outer surface of the catheter. It may be desirable to include more than one steering lumen, wherein each steering lumen may accommodate a separate tension cable, in order to enhance the steerability of the catheter. For example, an exemplary catheter may include a single guidewire lumen and two, three, or four separate steering lumens.

The catheters of the present systems further comprise a dock at the distal end of the catheter onto which a stent may be loaded. The dock is preferably integral with the rest of the catheter, and may simply comprise a distal portion of the catheter having a smaller diameter than the remainder of the catheter, or at least of the portion of the catheter that is located immediately adjacent to the dock. For example, whereas the outer diameter of the catheter (excluding the dock) may be about 0.25 cm to about 1.5 cm, the outer diameter of the dock may be from about 25% to about 75% of the diameter of the remainder of the catheter. Stated in absolute terms, the outer diameter of the dock may be about 0.10 cm to about 0.80 cm. The length of the dock is preferably at least as long as a stent in its fully compressed state (of which exemplary lengths are provided above in connection with the presently disclosed prostheses), and may be somewhat longer than a compressed stent. Stated in absolute terms, the length of the dock may be from about 4 cm to about 15 cm.

The dock may optionally comprise an inflatable balloon for expanding or assisting with the expansion of a stent that is loaded onto the dock. The use of inflatable balloons for the expansion of stents is well known among skilled artisans. Because such balloons are typically actuated at a desired time via the selective induction of fluid (liquid or gas) pressure, when the dock comprises an inflatable balloon, the catheter may further comprise a balloon lumen for supplying the fluid (for example, saline, water, or $CO_2$ gas) that is used to inflate the balloon. When inflated, the balloon may adopt any configuration that is suitable for assisting with the expansion of the stent; for example, the inflated balloon may be an elongated torus or a series of two or more tori that are distributed along the length of the dock.

The present systems further comprise at least one retractable compression sleeve for compressing at least a portion of the stent while the stent is loaded onto the dock. The compression sleeve is preferably in coaxial arrangement with the catheter, for example, functioning like a cannula or outer covering that translates over the catheter in a direction that is towards or away from the catheter's distal end. A stent may be loaded onto the dock in a compressed state, and the compression sleeve may be translated over the dock so that it passes over and encircles the compressed stent; in this way, the compression sleeve ensures that the stent remains compressed while loaded onto the dock. Specialized techniques may be required to load the stent onto the dock in a compressed state. With the compressed stent loaded onto the dock and at least one compression sleeve in coaxial arrangement with the dock and ensuring that the stent remains compressed, the distal end of the catheter may be delivered to the site of implantation, where the compression sleeve is eventually withdrawn and the stent thereby permitted to expand at the implantation site.

A compression sleeve may be made from any material that is biocompatible and is capable of functioning in the described manner. For example, a compression sleeve may be constructed from a rigid material so that it is not damaged or distorted by the outward radial force that is exerted by the compressed stent. The interior and/or exterior surfaces of the compression sleeve are preferably configured to result in a low coefficient of friction against any other component or physiological feature against which the sleeve may slide during use; this feature may be inherent in the material from which the sleeve is constructed, or may be imparted to the sleeve material by a low-friction coating. One exemplary material for use in constructing the compression sleeve is polytetrafluoroethylene (PTFE—sometimes produced under the trade name Teflon®). Any other suitable materials may be used, optionally coated on one or both of the inside and outside surfaces with PTFE or another material that is suitable for reducing friction.

A single compression sleeve may be used to compress the entire stent. In other instances, the system may comprise two or more compression sleeves; a second retractable compression sleeve, or other further compression sleeves, may be present for compressing a further portion of the stent when the stent is loaded onto the dock. For example, a first compression sleeve may be present and used to keep the middle region of the stent in the compressed state, and a second compression sleeve may be used to keep the upper and lower flanges of the stent in the compressed state. In such embodiments, when the stent is loaded onto the dock, both the first and second compression sleeves are positioned in coaxial arrangement with the dock, with the first compression sleeve being positioned directly over the stent, and the second compression sleeve being positioned over the first compression sleeve and the stent; withdrawal of second compression sleeve (e.g., by translation over the catheter in the direction away from the dock) results in the expansion of the flanges, and subsequent withdrawal of the first compression sleeve results in the expansion of the remainder of the stent. Because of the nature of the process of withdrawing the second compression sleeve, either the upper or lower flange will expand prior to the expansion of the other of the upper and lower flanges. The preceding process is described more fully below in connection with FIGS. 7-9. Expansion of the flanges by removal of the second compression sleeve prior to the expansion of the middle region by removal of the first compression sleeve results in the deployment of the flanges at the implantation site, which allows the stent to at least partially adhere to the implantation site before the middle region of the stent (containing the valve) is deployed.

The present systems further comprise a leading tip that is positioned distal to the dock portion of the catheter and that is for leading the catheter during the delivery process. The leading tip may be substantially conical, may be rounded at its distal end, or may have any other configuration that enhances the ease with which the tip and thereby the trailing catheter are directed through a subject's vasculature. Materials that may be used to form the leading tip may include any rigid, biocompatible, and preferably low-friction material. Examples include nylon, silastic, plastic, nitinol, stainless steel, cobalt/chromium alloy, cobalt/chromium/nickel alloy, nickel/chromium alloy, platinum, and platinum/iridium alloy. The leading tip may be securely yet removably attachable to the distal end of the dock, so that the stent can be loaded onto the dock prior to the attachment of the leading tip.

The systems according to the present disclosure also comprise a steering mechanism that is operably associated with the tension cable or cables and that is for deflecting the leading tip in at least one directional plane. The association between the steering mechanism and the tension cable or cables is described as operable because the steering mechanism makes use of its connection to the tension cable to deflect the leading tip. The use of tension cables for the deflection of a tension cable housing is readily understood among those skilled in the art. The steering mechanism may be any device that allows a user to manipulate the tension cable(s) and thereby the catheter in the intended manner—for example, an obturator knob, lever, dial, or any appropriate mechanism may be used. The deflection of the leading tip by use of the steering mechanism permits both the guidance of the catheter through a subject's vasculature (for example, to effect the downturn into the subject's ventricle) and the precision placement of the dock and stent at or near the site of implantation. The steering mechanism is typically used in conjunction with an appropriate imaging technology, such as fluoroscopy or echocardiography.

In yet another aspect, there are disclosed kits comprising a system comprising an at least partially self-expanding stent to an implantation site comprising: a catheter comprising a distal end and a proximal end; a guidewire lumen to permit the catheter to be translated along a guidewire; a steering lumen for accommodating a tension cable for steering the catheter; a dock at the distal end onto which the stent may be loaded; a retractable compression sleeve for compressing at least a portion of the stent while the stent is loaded onto the dock; a leading tip positioned distal to the dock for leading the catheter during delivery; and, a steering mechanism operably associated with the tension cable for deflecting the leading tip in at least one directional plane; and, at least one valve prosthesis comprising an at least partially self-expanding stent comprising a wire framework defining outer and interior surfaces, and upper and lower anchoring flanges interposed by a middle region, the stent having an unexpanded and an expanded state, and the lower anchoring flange having at least one geometric dimension that is greater than the corresponding dimension of the upper anchoring flange; and a valve comprising at least one leaflet fixedly attached to the interior surface of the stent.

Each of the attributes, components, materials, and the like that are described above with respect to the inventive valve prostheses and systems may be used in accordance with the prostheses and systems, respectively, that are included in the present kits.

The kits may further comprise one or more of the following additional components: instructions for use; replacement parts for any of the components of the system or prosthesis; and, tools for the repair of the system. In certain embodiments, the present kits comprise a plurality of valve prostheses, wherein the diameter of at least one of the prostheses in its expanded state is greater than the diameter of at least one other of the prostheses in its expanded state. Such embodiments account for the fact that user must choose a valve prosthesis that that is suitably sized in its expanded state for implantation in the particular site of interest within the particular patient at hand. The inner diameter of valve annuli vary within a particular patient, such that, for example, the diameter of the aortic valve annulus may be different from the diameter of the mitral valve annulus. Likewise, the inner diameter of a particular valve annulus, such as the mitral valve annulus, may vary from patient to patient, such that a first patient has a mitral valve annulus with a greater diamater than that of the mitral valve annulus of a second patient. Thus, a valve prosthesis must be selected to possess an appropriate diameter in its expanded state, wherein the propriety of a particular expanded diameter depends on the intended site of implantation and on the particular subject. It is therefore advantageous to include within a kit of the present disclosure at least two prostheses, wherein the diameter of at least one of the prostheses in its expanded state is greater than the diameter of at least one other of the prostheses in its expanded state, so that a choice may be made, depending on the relevant criteria, from among at least two different "sizes" of prosethesis.

The present kits may include at least two prostheses of which one possesses a different type of valve than at least one other prosthesis. For example, a particular kit may include three valve prostheses, of which two include a replacement mitral valve, and one includes a replacement aortic valve. The systems that are described herein for inclusion in the present kits may be used to deliver any type of prosthesis (including a prosthesis comprising any type of valve) to a site of implantation, and the inclusion of prostheses that respectively include different types of valves enables the user to select the prosthesis that is most suitable for the intended purpose.

Figure 7:
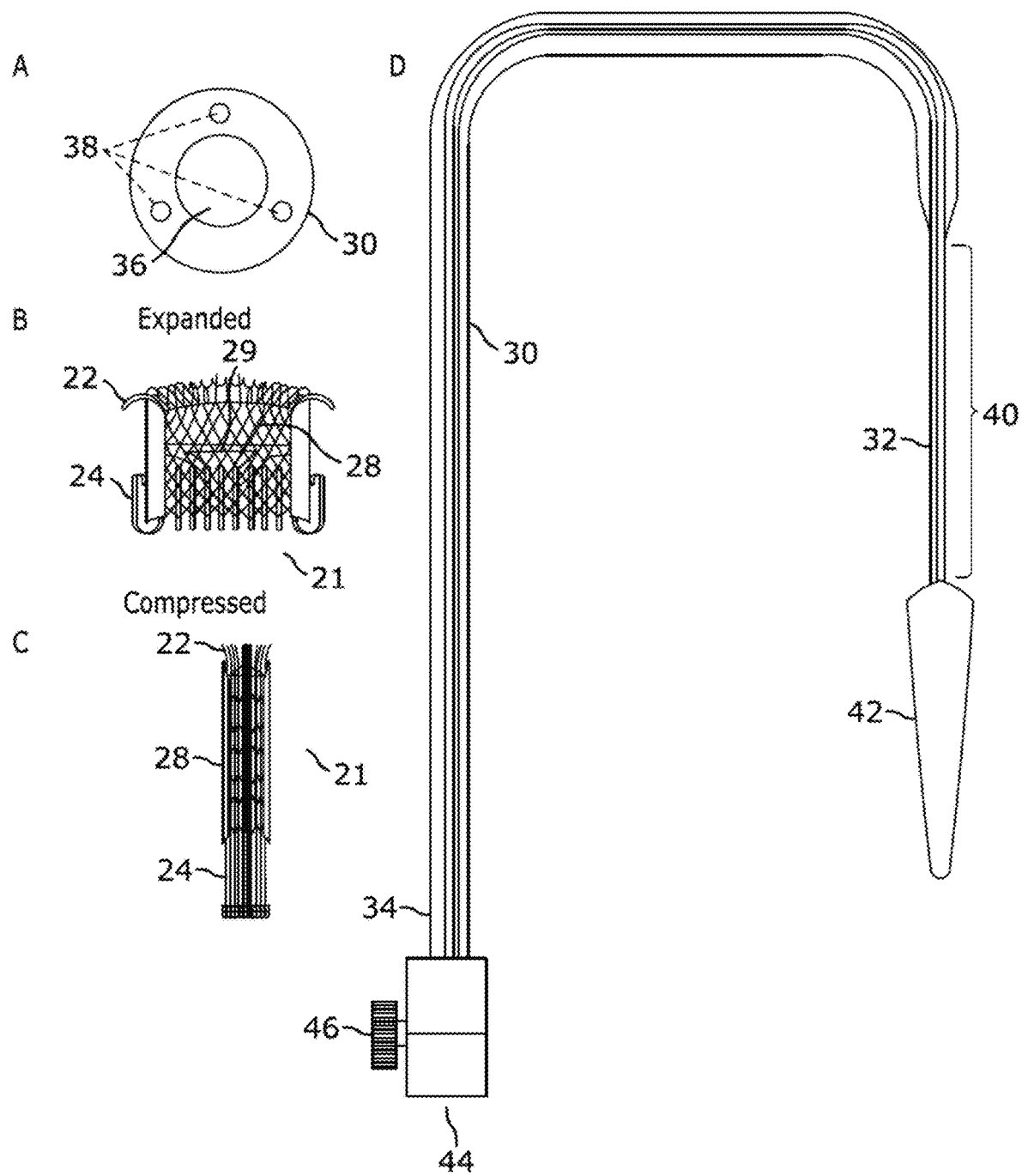
FIG. 7 depicts the components of an exemplary kit according to the present disclosure.

FIG. 7 depicts the components of an exemplary kit according to the present disclosure. As shown in FIG. 7D, the kit comprises system that includes a catheter 30 that has a distal end 32 and a proximal end 34. FIG. 7A provides a cross-sectional view of catheter 30 that reveals the guidewire lumen 36 and three steering lumens 38. Returning to FIG. 7D, dock 40 is at distal end 32 of catheter 30, and leading tip 42 is positioned distal to the dock 40. During use of the system, a prosthesis will be loaded onto dock 40. Steering mechanism 44 is located at proximal end 34 of catheter 30 and, in the depicted embodiment, comprises an obturator knob 46. The kit also includes a prosthesis comprising a stent 21 that comprises a wire framework, shown in its expanded state in FIG. 7B and in its compressed state in FIG. 7C. The wire framework of stent 21 defines upper 22 and lower 24 flanges interposed by a middle region 28. A valve 29 is fixedly attached to the interior of the stent 21.

The present disclosure also pertains to methods for delivering a valve prosthesis comprising an at least partially self-expanding stent to an implantation site comprising: (i) providing a system comprising a catheter comprising a distal end and a proximal end; a guidewire lumen to permit the catheter to be translated along a guidewire; a steering lumen for accommodating a tension cable for steering the catheter; a dock at the distal end onto which the stent may be loaded; a retractable compression sleeve for compressing at least a portion of the stent while the stent is loaded onto the dock; a leading tip positioned distal to the dock for leading the catheter during delivery; and, a steering mechanism operably associated with the tension cable for deflecting the leading tip in at least one directional plane; (ii) loading onto the dock the valve prosthesis; (iii) delivering a guidewire to the implantation site; (iv) translating the catheter over the guidewire so that the loaded valve prosthesis is positioned at the implantation site; (v) retracting the retractable compression sleeve to permit the stent to expand at the implantation site and to undock from the catheter; and, (vi) removing the catheter and the guidewire from the implantation site.

Each of the attributes, components, materials, and the like that are described above with respect to the inventive valve prostheses and systems may be used in accordance with the prostheses and systems, respectively, that are used in accordance with the present methods.

Figure 8:
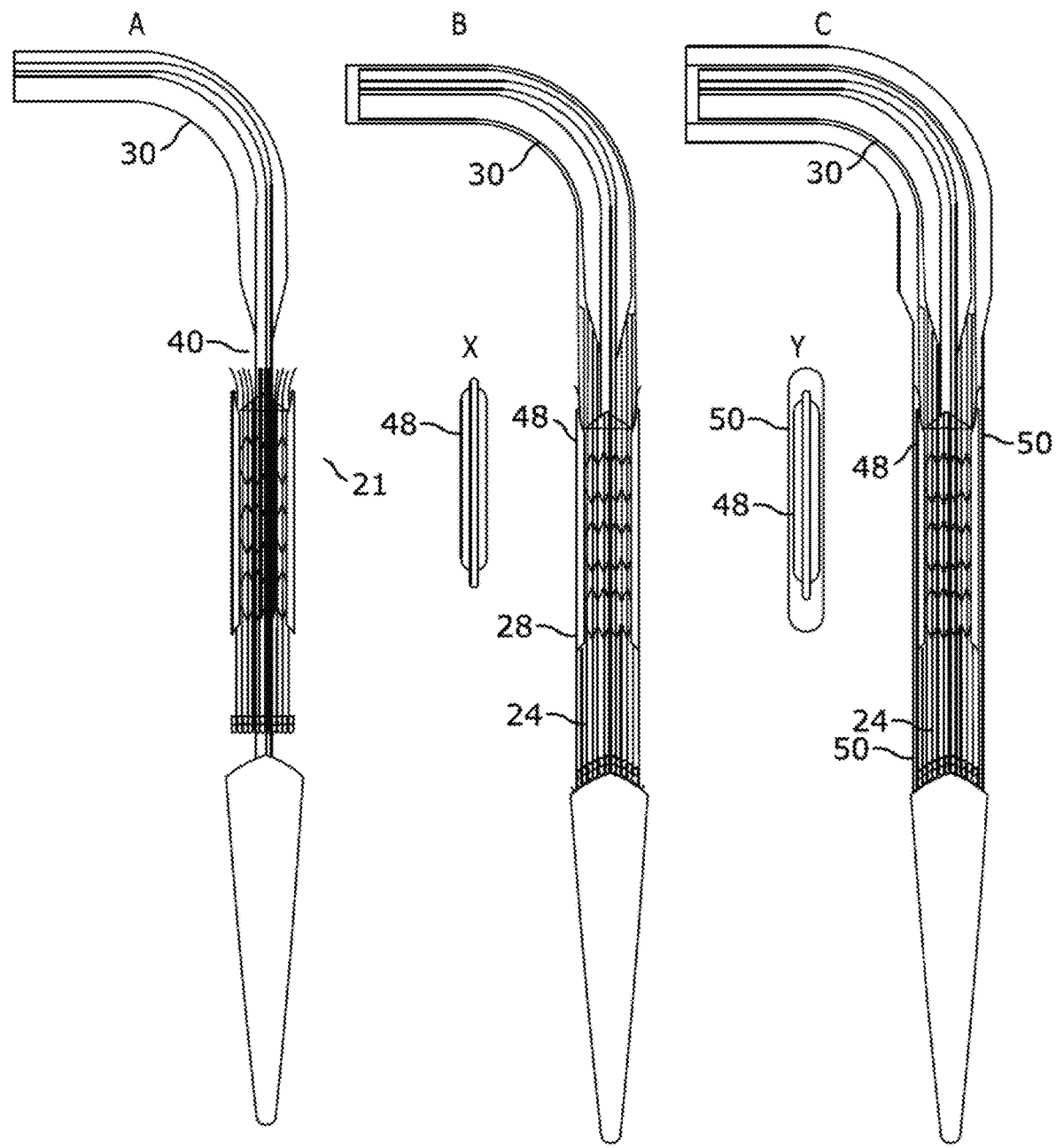
FIGS. 8-9 illustrate an example of how retractable compression sleeves may be used to compress a stent against the dock of a catheter during delivery to an implantation site, and to permit the stent to expand at the implantation site and undock from the catheter.
Figure 9:
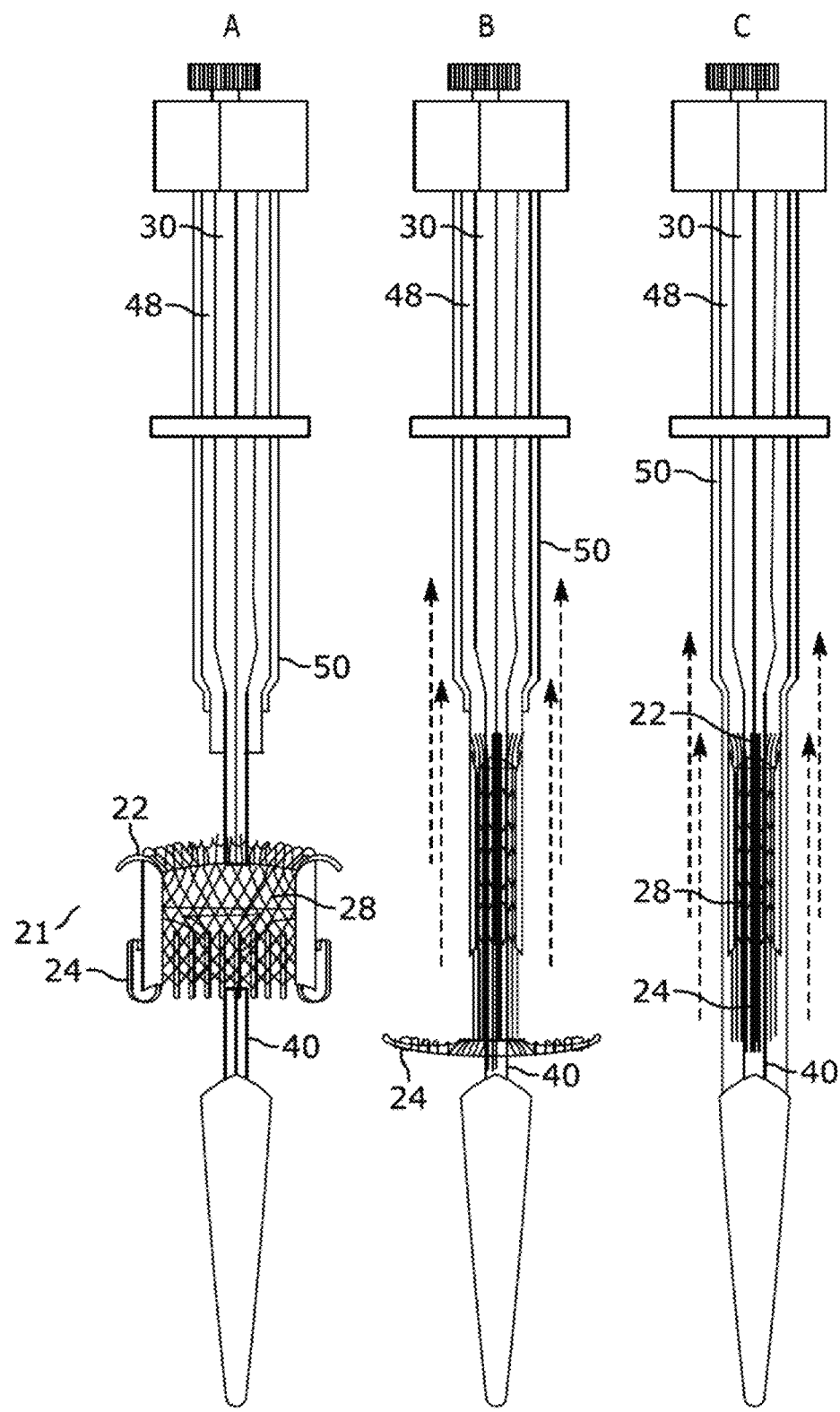

FIGS. 8-9 illustrate an example of how retractable compression sleeves 48, 50 may be used to compress a stent 21 against the dock 40 of a catheter 30 during delivery to an implantation site, and to permit the stent to expand at the implantation site and undock from the catheter 30. FIG. 8A depicts a compressed stent 21 that is mounted on dock 40 of a catheter 30; for simplicity, no compression sleeves are shown, even though the absence of a compression sleeve would ordinarily allow the stent 21 to expand. FIG. 8B shows how a first compression sleeve 48, shown as a dark gray layer (see illustrative inset X), is advanced over stent 21 and functions to compress the middle region 28 of stent 21. Lower flange 24 is not covered by first compression sleeve 48. In FIG. 8C, a second compression sleeve 50, shown as a lighter gray layer (see illustrative inset Y) is advanced over both first compression sleeve 48 and stent 21, this time including lower flange 24 of stent 21. Second compression sleeve 50 therefore ensures that lower flange 24 remains compressed during delivery of the distal end of catheter 30 to an implantation site.

FIG. 9A-C depicts in reverse order how the withdrawal of compression sleeves allows a prosthesis comprising a stent to expand in a controlled, sequential manner. In FIG. 9C, a first compression sleeve 48 and a second compression sleeve 50 are in place in coaxial arrangement over a stent that is mounted on the dock 40 of catheter 30; in concert, compression sleeves 48, 50 compress the middle region 28 of the stent and the flanges 22, 24 such that the stent remains mounted on dock 40. The light gray arrows in FIG. 9C indicate the direction in which second compression sleeve 50 is withdrawn over catheter 30 in order to proceed to the next step of the process of expanding the stent at the implantation site. FIG. 9B shows the results of withdrawing second compression sleeve 50: lower flange 24 has commenced to expand. The darker gray arrows in FIG. 9B indicate the direction in which first compression sleeve 48 is withdrawn over catheter 30 in order to permit expansion of each of the components of the stent. In FIG. 9A, first compression sleeve 48 has been fully withdrawn, and each of the lower flange 24, upper flange 22, and middle region 28 of the stent 21 have fully expanded. Lower flange 24 is bent back towards middle region 28, and any tissue that is interposed between these to components will be securely clamped.

In some embodiments of the present methods, the dock of the catheter may comprise an inflatable balloon, and following retraction of a retractable compression sleeve, the method may further comprise at least partially inflating the balloon to further expand the stent. Although the stent is at least partially self-expanding, it may be desireable to use a balloon to ensure that the stent reaches its maximally expanded state.

Figure 10:
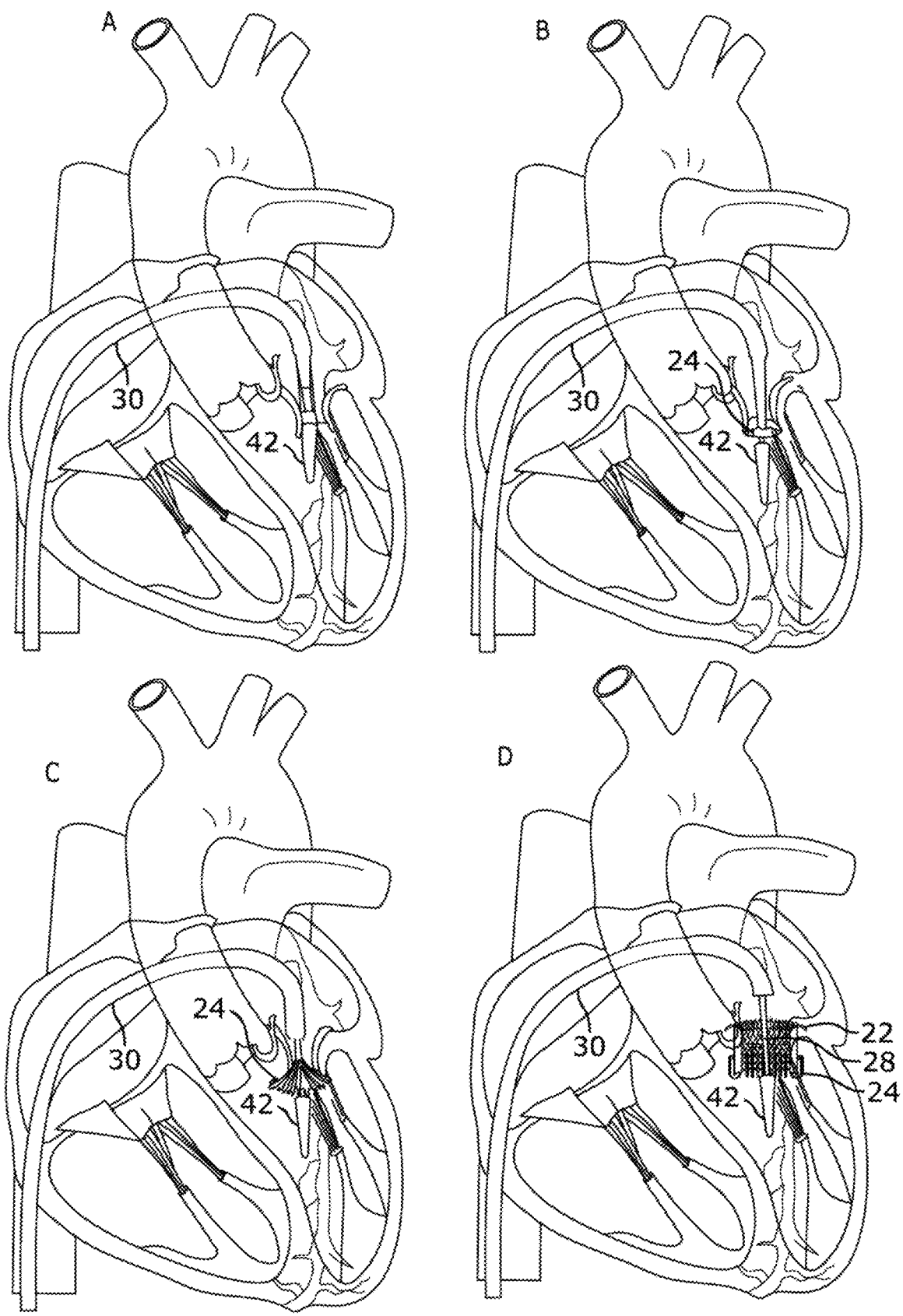
FIG. 10 illustrates how the process described in FIG. 9 will result in the implantation in situ of a valve prosthesis that comprises a wire framework.

FIG. 10 illustrates how the process described in FIG. 9 will result in the implantation in situ of a valve prosthesis that comprises a wire framework. In FIG. 10A, the implantation process is shown at the point where catheter 30 had been advanced to the implantation site (the mitral valve annulus), with leading tip 42 having been advanced past the valve annulus into the ventricle, and the dock, loaded with a compressed valve prosthesis, having been positioned within the valve annulus. FIG. 10B shows how the initial withdrawal of a compression sleeve from the loaded prosthesis results in the partial expansion and deployment of lower flange 24. In FIG. 10C, the compression sleeve has been withdrawn even further, such that a greater portion of lower flange 24 has expanded. FIG. 10D depicts the implantation process at the point when the compression sleeve has been fully withdrawn, lower flange 24 is bent back towards middle region 28, which is fully expanded and exerting radial force against the mitral valve annulus. Loose tissue on the ventricular side of the mitral valve annulus has been grasped by lower flange 24, and clamped between lower flange 24 and stent middle region 28. Upper flange 22 is also in the fully expanded state, has grasped loose tissue on the atrial side of the mitral valve annulus, and functions as a "cap" over the tissue on the atrial side of the annulus.

Example 1—Percutaneous Implantation via Transfemoral Approach

An exemplary delivery and implantation procedure may be performed as follows using the presently disclosed system for delivering a valve prosthesis, as well as a valve prosthesis according to the present disclosure.

First, the femoral vein (right or left) is accessed and a vascular sheath is inserted using the seldinger technique. The atrial septum is crossed via standard transseptal technique, and an atrial hole is created/enlarged via balloon dilation septostomy (10-15 mm angioplasty balloon)

A super-stiff guidewire is carefully shaped to and then positioned in the left ventricle through the newly created atrial hole. The femoral venous access site is made larger or "dilated up" with sequentially larger vascular dilators sized appropriately to match the diameter of the delivery system.

The valve prosthesis is compressed and positioned on the dock of the delivery system, and the system is otherwise prepared for insertion into the femoral vein. The loaded delivery catheter is advanced over the wire, into the femoral vein, through the venous system, across the atrial septal defect and then positioned at the level of the mitral annulus using ECHO (transesophageal and or Intracardiac) and fluoroscopic guidance. The steering mechanism is used to navigate the leading tip of the catheter through the vasculature and across the septum.

Once in position across the mitral annulus, deployment of the prosthesis is accomplished by sequentially withdrawing the containment sleeves, allowing the stent to expand. If necessary, the stent can be forcefully expanded to its nominal configuration by inflating a balloon located in the dock portion of the delivery catheter.

ECHO and fluoroscopic assessment is used to confirm position and stability of the device. If all looks stable, the delivery catheter is withdrawn from the body. A large vascular sheath is placed into the femoral vein to promote hemostasis. The atrial septal defect is closed using a percutaneous closure device (Amplatzer or Helex).

Example 2—Calculation of "Extraction Force"

In situ, the prostheses according to the present invention exert a number of different forces on the valve annulus and surrounding material. Such forces contribute to the unique ability of the prosthesis to remain anchored and properly positioned at the site of implantation. For example, the upper and lower flanges respectively bend back towards the middle region of the stent, and any tissue that is interposed between a flange and the middle region will be grasped by the flange and clamped between the flange and the middle region. The stent also exerts an outward radial force against the walls of the valve annulus. Although such forces can be difficult to measure individually, the force that is required to extract an implanted prosthesis represents one proxy of the aggregate the various forces that are exerted by the stent.

An experiment was conducted to measure the extraction force of an exemplary prosthesis. The test was conducted using a freshly excised sheep heart that was externally fixed in a custom-designed box that was built to hold the heart in a stable, upright position. First, a left atriotomy was performed to expose the mitral annulus. The prosthesis was then deployed into the mitral annulus under direct visualization. Sutures were looped through the atrial arms of the device, gathered into a central confluence and then knotted together being careful to keep each suture strand an equal length (much like the chords of a parachute come to a confluence at the back of the parachutist). Using a force gauge, the knotted sutures were pulled backward, using gradually increasing force to dislodge the device from the mitral annulus. The target for this process was that at least 15 Newtons of force would be required to extract the prosthesis. In fact, the prosthesis remained affixed to the annulus at 15 Newtons, and could not be extracted until the mitral valve and chordal tissue began to tear, at a point when greater than 20 Newtons was measured. Accordingly, the aggregate of the forces that were exerted by the prosthesis on the site of implantation enabled the device to adhere to the annulus even when significant extraction forces were applied.

Those skilled in the art also will readily appreciate that many additional modifications are possible in the exemplary embodiment without materially departing from the novel teachings and advantages of the invention. Accordingly, any such modifications are intended to be included within the scope of this invention as defined by the following exemplary claims.

What is claimed:

1. A prosthetic device comprising:
   an at least partially self-expanding stent adapted for percutaneous delivery and anchoring in a valve annulus, said stent comprising
   an expanded and an unexpanded state;
   a long axis;
   a middle region having first and second ends and comprising a framework that defines inner and outer surfaces;
   a lower flange portion at the first end of the middle region that comprises a first flange end that is attached to the middle region and an opposed second flange end that is spaced from the first end, wherein at least part of the lower flange portion includes a central portion that extends between the first flange end and the second flange end and that has a linear configuration when the stent is in the expanded state and when the stent is in the unexpanded state;
   when said stent is in the unexpanded state, the lower flange portion is oriented substantially along the long axis of the stent;
   when said stent transitions from the unexpanded state to the expanded state, the lower flange portion changes its orientation relative to the middle region of the stent; and
   the lower flange portion is adapted to anchor the stent within the valve annulus by grasping tissue at the ventricular side of the annulus by enfolding the tissue between the lower flange portion and the outer surface of the middle region as the stent transitions from the unexpanded state to the expanded state; and
   a valve comprising at least one leaflet fixedly attached to the inner surface of the middle region of the stent,
   wherein when the stent transitions from the unexpanded state to the expanded state, the lower flange portion transitions in space so that the second flange end of the lower flange portion moves closer to the middle region of the stent.

2. The prosthetic device according to claim 1, wherein the lower flange portion comprises a plurality of flange elements.

3. The prosthetic device according to claim 1, wherein the lower flange portion is oriented substantially parallel relative to the long axis of the stent when the stent is in the unexpanded state and is substantially parallel relative to the long axis of the stent when the stent is in the expanded state.

4. The prosthetic device according to claim 1, wherein the second flange end of the lower flange portion comprises an arc that extends from the central portion.

5. The prosthetic device according to claim 1, wherein the lower flange portion comprises an arc extending from the first flange end to the second flange end as the lower flange portion is being expanded, wherein the lower flange portion bends back toward the middle region of the stent, and
   wherein the lower flange portion is substantially parallel relative to the long axis of the stent when the stent is in the expanded state.

6. A prosthetic device comprising:
   an at least partially self-expanding stent adapted for percutaneous delivery and anchoring in a valve annulus, said stent comprising
   an expanded and an unexpanded state;
   a long axis;
   a middle region having first and second ends and comprising a framework that defines inner and outer surfaces;

a lower flange portion at the first end of the middle region that comprises a first flange end that is attached to the middle region and an opposed second flange end that is spaced from the first end;

when said stent is in the unexpanded state, the lower flange portion is oriented substantially along the long axis of the stent;

when said stent transitions from the unexpanded state to the expanded state, the lower flange portion changes its orientation relative to the middle region of the stent; and the lower flange portion is adapted to anchor the stent within the valve annulus by enfolding tissue at the ventricular side of the annulus between the lower flange portion and the outer surface of the middle region as the stent transitions from the unexpanded state to the expanded state; and a valve comprising at least one leaflet fixedly attached to the inner surface of the middle region of the stent, wherein, when the stent transitions from the unexpanded state to the expanded state, the lower flange portion transitions in space so that the second flange end of the lower flange portion bends back toward the middle region of the stent, and wherein at least part of the lower flange portion includes a central portion that extends between the first flange end and the second flange end and that has a linear configuration when the stent is in the expanded state and when the stent is in the unexpanded state.

7. The prosthetic device according to claim 6, wherein the lower flange portion comprises a plurality of flange elements.

8. The prosthetic device according to claim 6, wherein the lower flange portion is oriented substantially parallel relative to the long axis of the stent when the stent is in the unexpanded state and is substantially parallel relative to the long axis of the stent when the stent is in the expanded state.

9. The prosthetic device according to claim 6, wherein the second flange end of the lower flange portion comprises an arc that extends from the central portion.

10. The prosthetic device according to claim 6, wherein the lower flange portion comprises an arc extending from the first flange end to the second flange end as the lower flange portion is being expanded, wherein the lower flange portion bends back toward the middle region of the stent, and wherein the lower flange portion is substantially parallel relative to the long axis of the stent when the stent is in the expanded state.

11. A prosthetic device comprising:

an at least partially self-expanding stent adapted for percutaneous delivery and anchoring in a valve annulus, said stent comprising an expanded and an unexpanded state;

a long axis;

a middle region having first and second ends and comprising a framework that defines inner and outer surfaces;

a lower flange portion at the first end of the middle region that comprises a first flange end that is attached to the middle region and an opposed second flange end that is spaced from the first end;

when said stent is in the unexpanded state, the lower flange portion is oriented substantially along the long axis of the stent;

when said stent transitions from the unexpanded state to the expanded state, the lower flange portion changes its orientation relative to the middle region of the stent; and the lower flange portion is adapted to anchor the stent within the valve annulus by enfolding tissue at the ventricular side of the annulus between the lower flange portion and the outer surface of the middle region as the stent transitions from the unexpanded state to the expanded state; and a valve comprising at least one leaflet fixedly attached to the inner surface of the middle region of the stent, wherein, when the stent transitions from the unexpanded state to the expanded state, the lower flange portion transitions in space so that the second flange end of the lower flange portion bends back to a position that faces the middle region and is substantially parallel relative to the long axis of the stent, wherein the lower flange portion comprises an arc extending from the first flange end to the second flange end as the lower flange portion is being expanded, wherein the lower flange portion bends back toward the middle region of the stent, and wherein the lower flange portion is substantially parallel relative to the long axis of the stent when the stent is in the expanded state.

12. The prosthetic device according to claim 11, wherein at least part of the lower flange portion includes a central portion that extends between the first flange end and the second flange end and that has a linear configuration when the stent is in the expanded state and when the stent is in the unexpanded state.

13. The prosthetic device according to claim 11, wherein the lower flange portion comprises a plurality of flange elements.

14. The prosthetic device according to claim 11, wherein the lower flange portion is oriented substantially parallel relative to the long axis of the stent when the stent is in the unexpanded state.

15. The prosthetic device according to claim 11, wherein the second flange end of the lower flange portion comprises an arc that extends from the central portion.

16. A prosthetic device comprising:

an at least partially self-expanding stent adapted for percutaneous delivery and anchoring in a valve annulus, said stent comprising an expanded and an unexpanded state;

a long axis;

a middle region having first and second ends and comprising a framework that defines inner and outer surfaces;

a lower flange portion at the first end of the middle region that comprises a first flange end that is attached to the middle region and an opposed second flange end that is spaced from the first end;

when said stent is in the unexpanded state, the lower flange portion is oriented substantially along the long axis of the stent;

when said stent transitions from the unexpanded state to the expanded state, the lower flange portion changes its orientation relative to the middle region of the stent; and the lower flange portion is adapted to anchor the stent within the valve annulus by enfolding tissue at the ventricular side of the annulus between the lower flange portion and the outer surface of the middle region as the stent transitions from the unexpanded state to the expanded state; and a valve comprising at least one leaflet fixedly attached to the inner surface of the middle region of the stent, wherein, when the stent transitions from the unexpanded state to the expanded state, the lower flange portion transitions in space so that the second flange end of the lower flange portion bends back toward the middle region of the stent, and wherein the lower flange portion is oriented substantially parallel relative to the long axis of the stent when the stent is in the unexpanded state and is substantially parallel relative to the long axis of the stent when the stent is in the expanded state.

17. The prosthetic device according to claim 16, wherein the lower flange portion comprises a plurality of flange elements.

18. The prosthetic device according to claim 16, wherein the second flange end of the lower flange portion comprises an arc that extends from the central portion.

19. The prosthetic device according to claim 16, wherein the lower flange portion comprises an arc extending from the first flange end to the second flange end as the lower flange portion is being expanded, wherein the lower flange portion bends back toward the middle region of the stent, and wherein the lower flange portion is substantially parallel relative to the long axis of the stent when the stent is in the expanded state.

20. A prosthetic device comprising:

an at least partially self-expanding stent adapted for percutaneous delivery and anchoring in a valve annulus, said stent comprising an expanded and an unexpanded state;

a long axis;

a middle region having first and second ends and comprising a framework that defines inner and outer surfaces;

a lower flange portion at the first end of the middle region that comprises a first flange end that is attached to the middle region and an opposed second flange end that is spaced from the first end;

when said stent is in the unexpanded state, the lower flange portion is oriented substantially along the long axis of the stent;

when said stent transitions from the unexpanded state to the expanded state, the lower flange portion changes its orientation relative to the middle region of the stent; and the lower flange portion is adapted to anchor the stent within the valve annulus by enfolding tissue at the ventricular side of the annulus between the lower flange portion and the outer surface of the middle region as the stent transitions from the unexpanded state to the expanded state; and a valve comprising at least one leaflet fixedly attached to the inner surface of the middle region of the stent, wherein, when the stent transitions from the unexpanded state to the expanded state, the lower flange portion transitions in space so that the second flange end of the lower flange portion bends back toward the middle region of the stent, wherein the lower flange portion comprises an arc extending from the first flange end to the second flange end as the lower flange portion is being expanded, wherein the lower flange portion bends back toward the middle region of the stent, and wherein the lower flange portion is substantially parallel relative to the long axis of the stent when the stent is in the expanded state.

21. The prosthetic device according to claim 20, wherein the lower flange portion comprises a plurality of flange elements.

22. The prosthetic device according to claim 20, wherein the second flange end of the lower flange portion comprises an arc that extends from the central portion.

* * * * *